United States Patent
Carfi et al.

(10) Patent No.: US 10,364,273 B2
(45) Date of Patent: Jul. 30, 2019

(54) CYTOMEGALOVIRUS ANTIGENS

(71) Applicant: GLAXOSMITHKLINE BIOLOGICALS SA, Rixensart (BE)

(72) Inventors: Andrea Carfi, Cambridge, MA (US); Sumana Chandramouli, Cambridge, MA (US); Ethan C. Settembre, Cambridge, MA (US)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 15/533,483

(22) PCT Filed: Dec. 7, 2015

(86) PCT No.: PCT/IB2015/059420
§ 371 (c)(1),
(2) Date: Jun. 6, 2017

(87) PCT Pub. No.: WO2016/092460
PCT Pub. Date: Jun. 16, 2016

(65) Prior Publication Data
US 2018/0265551 A1 Sep. 20, 2018

(30) Foreign Application Priority Data
Dec. 8, 2014 (EP) .................... 14196854

(51) Int. Cl.
| C07K 14/005 | (2006.01) |
| A61K 39/12 | (2006.01) |
| A61K 39/245 | (2006.01) |
| A61K 39/00 | (2006.01) |

(52) U.S. Cl.
CPC ............ *C07K 14/005* (2013.01); *A61K 39/12* (2013.01); *A61K 39/245* (2013.01); *A61K 39/00* (2013.01); *C12N 2710/16122* (2013.01); *C12N 2710/16134* (2013.01)

(58) Field of Classification Search
CPC .... C07K 14/005; A61K 39/12; A61K 39/245; A61K 39/00; A61K 35/76; C12N 2710/16134; C12N 2710/16122; C12N 7/00; C12N 2710/16633; A61P 37/04; A61P 31/22
See application file for complete search history.

(56) References Cited

U.S. PATENT DOCUMENTS

| 6,100,064 A * | 8/2000 | Burke ................. C07K 14/005 435/320.1 |
| 2006/0204473 A1* | 9/2006 | Blatt .................... C07K 14/555 424/85.5 |
| 2010/0273991 A1* | 10/2010 | Luk .................. A61K 39/39591 530/391.1 |
| 2013/0216613 A1* | 8/2013 | Baudoux ............. A61K 39/245 424/450 |
| 2016/0296619 A1* | 10/2016 | Orlinger ................ A61K 39/12 |

FOREIGN PATENT DOCUMENTS

| WO | 200005389 A2 | 2/2000 |
| WO | 2012049317 A2 | 4/2012 |

OTHER PUBLICATIONS

Solá RJ, Griebenow K. Effects of glycosylation on the stability of protein pharmaceuticals. J Pharm Sci. Apr. 2009;98(4):1223-45.*
Pantophlet R, Wilson IA, Burton DR. Hyperglycosylated mutants of human immunodeficiency virus (HIV) type 1 monomeric gp120 as novel antigens for HIV vaccine design. J Virol. May 2003;77(10):5889-901.*
Lin SC, Lin YF, Chong P, Wu SC. Broader neutralizing antibodies against H5N1 viruses using prime-boost immunization of hyperglycosylated hemagglutinin DNA and virus-like particles. PLoS One. 2012;7(6):e39075. Epub Jun. 13, 2012.*
Boehme et al., Human cytomegalovirus envelope glycoproteins B and H are necessary for TLR2 activation in permissive cells. J Immunol. Nov. 15, 2006;177(10):7094-102.
Britt et al., Cell surface expression of human cytomegalovirus (HCMV) gp55-116 (gB): use of HCMV-recombinant vaccinia virus-infected cells in analysis of the human neutralizing antibody response. J Virol. Mar. 1990;64(3):1079-85.
Chandramouli et al., Structure of HCMV glycoprotein B in the postfusion conformation bound to a neutralizing human antibody. Nat Commun. Sep. 14, 2015;6:8176.
Go et al., A cytomegalovirus vaccine for transplantation: are we closer? J Infect Dis. Jun. 15, 2008;197(12):1631-3.
Heldwein et al., Crystal structure of glycoprotein B from herpes simplex virus 1. Science. Jul. 14, 2006;313(5784):217-20.
Ohlin et al., Fine specificity of the human immune response to the major neutralization epitopes expressed on cytomegalovirus gp58/116 (gB), as determined with human monoclonal antibodies. J Virol. Feb. 1993;67(2):703-10.
Pötzsch et al., B cell repertoire analysis identifies new antigenic domains on glycoprotein B of human cytomegalovirus which are target of neutralizing antibodies. PLoS Pathog. Aug. 2011;7(8):e1002172.
Sharma et al., HCMV gB shares structural and functional properties with gB proteins from other herpesviruses. Virology. Jan. 20, 2013;435(2):239-49.
Singh et al., Characterization of a panel of insertion mutants in human cytomegalovirus glycoprotein B. J Virol. Feb. 2000;74(3):1383-92.

(Continued)

*Primary Examiner* — Rachel B Gill

(57) ABSTRACT

The invention generally relates to recombinant human cytomegalovirus (CMV) gB proteins and immunogenic fragments thereof, which do not comprise a transmembrane (TM) domain; and comprise one or more mutations that reduce the aggregation between the monomeric trimers of gB, and/or adhesion of the monomeric trimer of gB to the host cell.

17 Claims, 4 Drawing Sheets
Specification includes a Sequence Listing.

(56) References Cited

OTHER PUBLICATIONS

Spindler et al., Characterization of a discontinuous neutralizing epitope on glycoprotein B of human cytomegalovirus. J Virol. Aug. 2013;87(16):8927-39.

Wiegers et al., Identification of a neutralizing epitope within antigenic domain 5 of glycoprotein B of human cytomegalovirus. J Virol. Jan. 2015;69(1):361-72.

Wille et al., Human cytomegalovirus (HCMV) glycoprotein gB promotes virus entry in trans acting as the viral fusion protein rather than as a receptor-binding protein. MBio. Jun. 4, 2013;4(3):e00332-13.

International Search Report and Written Opinion for Application No. PCT/IB2015/059420, dated Sep. 30, 2016.

* cited by examiner

Figure 1

SEQUENCE LISTING

```
<160> NUMBER OF SEQ ID NOS: 21

<210> SEQ ID NO 1
<211> LENGTH: 907
<212> TYPE: PRT
<213> ORGANISM: Human cytomegalovirus

<400> SEQUENCE: 1

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110
```

```
Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
            130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
                180                 185                 190

Ile Ala Gly Thr Val Phe Val Ala Tyr His Arg Asp Ser Tyr Glu Asn
                195                 200                 205

Lys Thr Met Gln Leu Met Pro Asp Asp Tyr Ser Asn Thr His Ser Thr
            210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
            275                 280                 285

Tyr Phe Gly Glu Asn Ala Asp Lys Phe Ile Phe Pro Asn Tyr Thr
            290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
            370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
                420                 425                 430

Gly Ile Lys Gln Lys Ser Leu Val Glu Leu Glu Arg Leu Ala Asn Arg
            435                 440                 445

Ser Ser Leu Asn Leu Thr His Asn Arg Thr Lys Arg Ser Thr Asp Gly
            450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
```

```
         530                 535                 540
Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905
```

<210> SEQ ID NO 2
<211> LENGTH: 906
<212> TYPE: PRT
<213> ORGANISM: Human cytomegalovirus

<400> SEQUENCE: 2

-continued

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
            35                  40                  45

Thr Arg Ser Val Tyr Ser Gln His Val Thr Ser Glu Ala Val Ser
        50                  55                  60

His Arg Ala Asn Glu Thr Ile Tyr Asn Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
            245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
        290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
            325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
            370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
            405                 410                 415

Asn Val Ser Val Phe Glu Thr Ser Gly Gly Leu Val Val Phe Trp Gln
```

```
            420                 425                 430
Gly Ile Lys Gln Lys Ser Leu Val Glu Leu Glu Arg Leu Ala Asn Arg
                435                 440                 445
Ser Ser Leu Asn Ile Thr His Arg Thr Arg Arg Ser Thr Ser Asp Asn
450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
                500                 505                 510
Leu Glu Val Phe Lys Glu Leu Ser Lys Ile Asn Pro Ser Ala Ile Leu
                515                 520                 525
Ser Ala Ile Tyr Asn Lys Pro Ile Ala Ala Arg Phe Met Gly Asp Val
                530                 535                 540
Leu Gly Leu Ala Ser Cys Val Thr Ile Asn Gln Thr Ser Val Lys Val
545                 550                 555                 560
Leu Arg Asp Met Asn Val Lys Glu Ser Pro Gly Arg Cys Tyr Ser Arg
                565                 570                 575
Pro Val Val Ile Phe Asn Phe Ala Asn Ser Ser Tyr Val Gln Tyr Gly
                580                 585                 590
Gln Leu Gly Glu Asp Asn Glu Ile Leu Leu Gly Asn His Arg Thr Glu
                595                 600                 605
Glu Cys Gln Leu Pro Ser Leu Lys Ile Phe Ile Ala Gly Asn Ser Ala
                610                 615                 620
Tyr Glu Tyr Val Asp Tyr Leu Phe Lys Arg Met Ile Asp Leu Ser Ser
625                 630                 635                 640
Ile Ser Thr Val Asp Ser Met Ile Ala Leu Asp Ile Asp Pro Leu Glu
                645                 650                 655
Asn Thr Asp Phe Arg Val Leu Glu Leu Tyr Ser Gln Lys Glu Leu Arg
                660                 665                 670
Ser Ser Asn Val Phe Asp Leu Glu Glu Ile Met Arg Glu Phe Asn Ser
                675                 680                 685
Tyr Lys Gln Arg Val Lys Tyr Val Glu Asp Lys Val Val Asp Pro Leu
                690                 695                 700
Pro Pro Tyr Leu Lys Gly Leu Asp Asp Leu Met Ser Gly Leu Gly Ala
705                 710                 715                 720
Ala Gly Lys Ala Val Gly Val Ala Ile Gly Ala Val Gly Gly Ala Val
                725                 730                 735
Ala Ser Val Val Glu Gly Val Ala Thr Phe Leu Lys Asn Pro Phe Gly
                740                 745                 750
Ala Phe Thr Ile Ile Leu Val Ala Ile Ala Val Val Ile Ile Thr Tyr
                755                 760                 765
Leu Ile Tyr Thr Arg Gln Arg Arg Leu Cys Thr Gln Pro Leu Gln Asn
                770                 775                 780
Leu Phe Pro Tyr Leu Val Ser Ala Asp Gly Thr Thr Val Thr Ser Gly
785                 790                 795                 800
Ser Thr Lys Asp Thr Ser Leu Gln Ala Pro Pro Ser Tyr Glu Glu Ser
                805                 810                 815
Val Tyr Asn Ser Gly Arg Lys Gly Pro Gly Pro Pro Ser Ser Asp Ala
                820                 825                 830
Ser Thr Ala Ala Pro Pro Tyr Thr Asn Glu Gln Ala Tyr Gln Met Leu
                835                 840                 845
```

```
Leu Ala Leu Ala Arg Leu Asp Ala Glu Gln Arg Ala Gln Gln Asn Gly
        850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
            900                 905

<210> SEQ ID NO 3
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Asp Trp Leu Lys Ala Phe Tyr Asp Lys Val Ala Glu Lys Leu Lys Glu
1               5                   10                  15

Ala Phe Leu Ala
            20

<210> SEQ ID NO 4
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Glu Leu Leu Glu Lys Trp Lys Glu Ala Leu Ala Ala Leu Ala Glu Lys
1               5                   10                  15

Leu Lys

<210> SEQ ID NO 5
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Phe Trp Leu Lys Ala Phe Tyr Asp Lys Val Ala Glu Lys Leu Lys Glu
1               5                   10                  15

Ala Phe

<210> SEQ ID NO 6
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asp Trp Leu Lys Ala Phe Tyr Asp Lys Val Ala Glu Lys Leu Lys Glu
1               5                   10                  15
```

```
Ala Phe Arg Leu Thr Arg Lys Arg Gly Leu Lys Leu Ala
            20                  25
```

```
<210> SEQ ID NO 7
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Asp Trp Leu Lys Ala Phe Tyr Asp Lys Val Ala Glu Lys Leu Lys Glu
1               5                   10                  15

Ala Phe
```

```
<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 8

His His His His His His
1               5
```

```
<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Asp Tyr Lys Asp Asp Asp Asp Lys
1               5
```

```
<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ala Trp Arg His Pro Gln Phe Gly Gly
1               5
```

```
<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Trp Ser His Pro Gln Phe Glu Lys
```

```
1               5

<210> SEQ ID NO 12
<211> LENGTH: 5
<212> TYPE: PRT
<213> ORGANISM: Human cytomegalovirus

<400> SEQUENCE: 12

Arg Gly Ser Thr Trp
1               5

<210> SEQ ID NO 13
<211> LENGTH: 8
<212> TYPE: PRT
<213> ORGANISM: Human cytomegalovirus

<400> SEQUENCE: 13

Arg Gly Ser Thr Asn Gly Thr Trp
1               5

<210> SEQ ID NO 14
<211> LENGTH: 4
<212> TYPE: PRT
<213> ORGANISM: Human cytomegalovirus

<400> SEQUENCE: 14

Trp Leu Tyr Arg
1

<210> SEQ ID NO 15
<211> LENGTH: 7
<212> TYPE: PRT
<213> ORGANISM: Human cytomegalovirus

<400> SEQUENCE: 15

Trp Leu Tyr Asn Gly Thr Arg
1               5

<210> SEQ ID NO 16
<211> LENGTH: 5
<212> TYPE: PRT
<213> ORGANISM: Human cytomegalovirus

<400> SEQUENCE: 16

Asn Gly Ser Thr Trp
1               5

<210> SEQ ID NO 17
<211> LENGTH: 5
<212> TYPE: PRT
<213> ORGANISM: Human cytomegalovirus

<400> SEQUENCE: 17

Arg Asn Ser Thr Trp
1               5

<210> SEQ ID NO 18
<211> LENGTH: 5
<212> TYPE: PRT
<213> ORGANISM: Human cytomegalovirus

<400> SEQUENCE: 18

Glu Gly Glu Thr Trp
1               5
```

```
<210> SEQ ID NO 19
<211> LENGTH: 5
<212> TYPE: PRT
<213> ORGANISM: Human cytomegalovirus

<400> SEQUENCE: 19

Glu Gly Glu Glu Trp
1               5

<210> SEQ ID NO 20
<211> LENGTH: 4
<212> TYPE: PRT
<213> ORGANISM: Human cytomegalovirus

<400> SEQUENCE: 20

Arg Thr Lys Arg
1

<210> SEQ ID NO 21
<211> LENGTH: 4
<212> TYPE: PRT
<213> ORGANISM: Human cytomegalovirus

<400> SEQUENCE: 21

Arg Gln Arg Arg
1
```

CYTOMEGALOVIRUS ANTIGENS

REFERENCE TO SEQUENCE LISTING SUBMITTED ELECTRONICALLY VIA EFS-WEB

The content of the electronically submitted sequence listing (Name: "VN56317 PCT Seq Lis"; 19,648 bytes; and Date of Creation: Mar. 9, 2016) was originally submitted in the International Application No. PCT/IB2015/059420, filed Dec. 7, 2015, and is incorporated herein by reference in its entirety.

FIELD OF THE INVENTION

This invention relates to cytomegalovirus (CMV) proteins suitable for vaccine uses.

BACKGROUND OF THE INVENTION

Human cytomegalovirus (HCMV) causes widespread, persistent human infections that vary with the age and immunocompetence of the host. It can remain latent throughout the lifetime of the host with sporadic reactivation events. The primary infection of hosts with a functional immune system is associated with mild symptoms although it may progress with fever, hepatitis, splenomegaly and a mononucleosis-like disease. In contrast, when primary infection or reactivation occurs in immunocompromised or immunodeficient hosts, they often experience life-threatening diseases, including pneumonia, hepatitis, retinitis and encephalitis (Sinclair and Sissons, J. Gen. Virol. 87:1763-1779, 2006). HCMV infection has been recognized for its association with three different populations: neonates with immature immune systems; transplant recipients with impaired immune systems due to the use of drugs and HIV-infected patients with compromised immune systems due to the decline of CD4+ T cells.

HCMV can be particularly devastating in neonates, causing defects in neurological development. In the industrialized countries, intrauterine viral infection is most common. Estimates suggest that between 0.6% and 0.7% (depending on the seroprevalence of the population examined) of all new neonates are infected in utero (Dollard et al., Rev. Med. Virol., 17(5):355-363, 2007). In the United States alone, this corresponds to approximately 40,000 new infections each year. Around 1.4% of intrauterine CMV infections occur from transmission by women with established infection. New maternal infection occurs in 0.7 to 4.1% of pregnancies and is transmitted to the fetus in about 32% of cases. Around 90% of infected infants are asymptomatic at birth and most will develop serious consequences of the infection over the course of several years, including mental retardation and hearing loss. Other infected children show symptomatic HCMV disease with symptoms of irreversible central nervous system involvement in the form of microencephaly, encephalitis, seizures, deafness, upper-motor neuron disorders and psychomotor retardation (Kenneson et al., Rev. Med. Virol., 17(4):253-276, 2007). In sum, approximately 8,000 children in the United States develop virus-related neurological disease each year. Congenital infection is the major driving force behind efforts to develop an HCMV vaccine.

CMV envelope glycoproteins gB, gH, gL, gM and gN represent attractive vaccine candidates as they are expressed on the viral surface and can elicit protective virus-neutralizing humoral immune responses.

Some CMV vaccine strategies have targeted the major surface glycoprotein B (gB), which can induce a dominant antibody response (Go and Pollard, J Infect Dis. 2008; 197:1631-1633). Glycoprotein B (gB) is a trimeric protein that is highly conserved among the different strains of HCMV, as well as among other Herpesviruses, such as Herpes Simplex Virus (HSV) and Epstein Barr Virus (EBV). It belongs to the Class III viral fusion proteins and plays a critical role in the viral replicative cycle by fusing the viral membrane with that of the target cell, facilitating delivery of the viral genome into the cytoplasm. Clinical trials are in progress to evaluate the efficacy of subunit as well as virus-like particle vaccine candidates incorporating various forms of HCMV gB. CMV glycoprotein gB can induce a neutralizing antibody response, and sera from CMV-positive patients is largely composed of antibodies directed against gB (Britt, Journal of Virology 64:1079-1085, 1990).

WO/2012/049317 discloses CMV gB polypeptide comprising a fusion loop 1 (FL1) domain and a fusion loop 2 (FL2) domain, wherein at least one of the FL1 and FL2 domains comprises at least one amino acid deletion or substitution. Examples show that the percentage of gB trimers was around 70%.

A need exists for an effective vaccine that is targeted to the CMV glycoprotein gB and for immunization methods that produce better immune responses.

SUMMARY OF THE INVENTION

As disclosed and exemplified herein, certain mutations can be introduced into the cytomegalovirus (CMV) gB protein (or an immunogenic fragment thereof), in particular, to facilitate the recombinant production and purification of recombinant gB protein for vaccine uses. The inventors recognized that a wild type gB protein ectodomain, which naturally forms a monomeric trimer, has an exposed hydrophobic surface that may render recombination expression of the protein, and subsequent secretion from the host cell, very difficult. Particularly useful mutations are those that (i) at least partially mask said hydrophobic surface, (ii) reduce the overall hydrophobicity of said hydrophobic surface, or (iii) both.

Accordingly, in one aspect, the invention provides a cytomegalovirus (CMV) gB protein, or an immunogenic fragment thereof, wherein (i) said gB protein, or immunogenic fragment thereof, does not comprise a transmembrane (TM) domain; and (ii) said gB protein, or immunogenic fragment thereof, comprises a mutation that results in a glycosylation site within hydrophobic surface 1 (amino acid residues 154-160 and 236-243). Preferably, said glycosylation site is an N-glycosylation site comprising an N-X-S/T/C motif, wherein X is any amino acid residue (but preferably not proline).

In another aspect, the invention provides a recombinant cytomegalovirus (CMV) gB protein, or an immunogenic fragment thereof, wherein (i) said gB protein, or immunogenic fragment thereof, does not comprise a transmembrane (TM) domain; and (ii) said gB protein, or immunogenic fragment thereof, comprises a mutation that results in a glycosylation site, wherein said glycosylation site is (1) within hydrophobic surface 2 (amino acid residues 145-167 and 230-252); or (2) at a residue that is within 20 angstroms from fusion loop 1 (FL1) (amino acid residues 155-157) and/or fusion loop 2 (FL2) (amino acid residues 240-242).

In another aspect, the invention provides a recombinant cytomegalovirus (CMV) gB protein, or an immunogenic fragment thereof, wherein (i) said gB protein, or immunogenic fragment thereof, does not comprise a transmembrane (TM) domain; and (ii) said gB protein, or immunogenic fragment thereof, comprises a mutation within hydrophobic surface 1 (amino acid residues 154-160 and 236-243), wherein said mutation results in a reduction of overall hydrophobicity index of said hydrophobic surface 1; wherein said mutation is not a deletion or substitution of an amino acid in fusion loop 1 (FL1) (or in fusion loop 2 (FL2).

In another aspect, the invention provides a cytomegalovirus (CMV) gB protein, or an immunogenic fragment thereof, wherein (i) said gB protein, or immunogenic fragment thereof, does not comprise a transmembrane (TM) domain; (ii) said gB protein, or immunogenic fragment thereof, comprises an ectodomain; and (iii) said gB protein, or immunogenic fragment thereof, comprises a heterologous sequence that is at least 12 residues long at the C-terminus. In some aspects, the gB protein may be a fusion protein wherein the heterologous sequence is fused at the C-terminus of the ectodomain. In some aspects, the heterologous sequence may be an amphipathic peptide.

Also provided herein are immunogenic compositions comprising CMV gB proteins and immunogenic fragments thereof, as described herein. The immunogenic compositions may comprise an immunological adjuvant, and/or another CMV antigen.

Also provided herein are nucleic acids encoding CMV gB and immunogenic fragments thereof, as described herein. The nucleic acid may be used as a nucleic acid-based vaccine (e.g., a self-replicating RNA molecule encoding the gB or an immunogenic fragment thereof). The nucleic acid may also be used for recombinant production of gB protein.

The invention also provides a host cell comprising the nucleic acids described herein. The nucleic acids can express a gB protein (or an immunogenic fragment thereof), and preferably form a monomeric trimer. Preferably, the monomeric trimer can be secreted from the host cell. Preferred host cells are mammalian host cells, such as CHO cells or HEK-293 cells.

The invention also provides a cell culture comprising the host cell described herein. Preferably, the culture is at least 20 liters in size, and/or the yield of gB protein (or an immunogenic fragment thereof) is at least 0.1 g/L.

The invention also provides a method of inducing an immune response against cytomegalovirus (CMV), comprising administering to a subject in need thereof an immunologically effective amount of the gB protein (or an immunogenic fragment thereof) described herein. The invention also provides a method of inhibiting cytomegalovirus (CMV) entry into a cell, comprising contacting the cell with the gB protein (or an immunogenic fragment thereof) described herein.

Also provided are use of the compositions described herein for inducing an immune response against cytomegalovirus (CMV), and use of the compositions described herein in the manufacture of a medicament for inducing an immune response against cytomegalovirus (CMV).

BRIEF DESCRIPTION OF THE FIGURES

FIG. 1 is a schematic representation of the CMV gB protein from the Merlin strain. TM: transmembrane domain; Cyto: cytoplasmic domain; SP: signal peptide; MPR: membrane proximal region; I: Domain I; II: Domain II; Ill: Domain III; IV: Domain IV; V: Domain V. The indicated numbers refer to the position of amino acid residues of CMV gB from the Merlin strain and set forth in SEQ ID NO: 1.

DETAILED DESCRIPTION OF THE INVENTION

1. Overview

Figure 2:
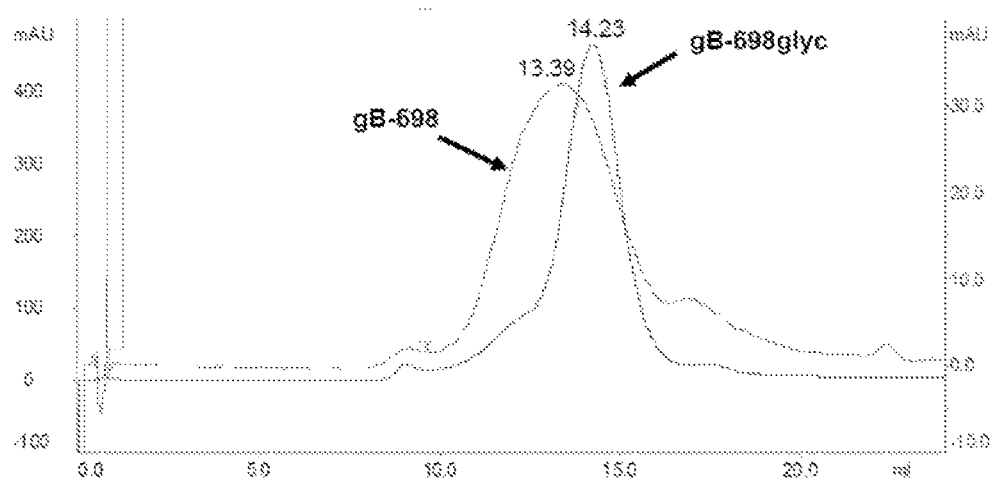
FIG. 2 shows the result of size exclusion chromatography. The figure shows that gB-698, with fusion loop mutations but without glycosylation, formed dimeric trimers, whereas gB-698glyc mutant did not form dimeric trimers even at high protein concentration.

As described and exemplified herein, the inventors have discovered that certain mutations can be introduced to the cytomegalovirus (CMV) gB protein (or an immunogenic fragment thereof, such as the ectodomain) to facilitate the recombinant production of this protein.

In general, the CMV gB protein forms a monomeric trimer (comprising three gB proteins, also referred to as subunits) that can be used as an antigen against CMV. However, the monomeric trimer comprises an exposed hydrophobic surface, which can cause significant problems in both antigen production and purification. For example, the hydrophobic surface can cause aggregation of recombinantly produced gB protein (e.g., two monomeric trimers can form a dimeric timer via the hydrophobic surface, which may cause production problems). The hydrophobic surface also causes the monomeric gB trimer to adhere to the host cell (e.g., to cell membrane, ER membrane, other hydrophobic proteins, aggregated proteins, etc.). The inventors have discovered that modifying this hydrophobic surface can greatly facilitate the production and subsequent purification of the gB antigen.

As disclosed herein, the inventors solved the crystal structure of the CMV gB, in monomeric trimer form, complexed with an anti-gB antibody (Fab). Based on the crystal structure, the inventors identified several categories of mutations that can reduce the aggregation between the monomeric trimers, and/or adhesion of the monomeric trimer to the host cell (e.g., to cell membrane, ER membrane, other hydrophobic proteins, aggregated proteins, etc.). In particular, the mutations in general also allow the monomeric trimer to be secreted from a host cell, thereby significantly improving the efficiency of production processes.

Based on the crystal structure, the inventors discovered that several categories of mutations can be introduced.

First, a glycosylation site can be introduced in a narrower hydrophobic surface, referred herein as "hydrophobic surface 1" (which comprises amino acid residues 154-160 and 236-243). Without wishing to be bound by theory, it is believed that the attachment of a glycan moiety can create a physical barrier (as well as a more hydrophilic surface), which reduces the undesired aggregation of monomeric trimers, and the undesired adhesion of a monomeric trimer to the host cell (e.g., to cell membrane, ER membrane, other hydrophobic proteins, aggregated proteins, etc.) through the hydrophobic surface. The mutation allows the gB protein (or immunogenic fragment thereof) to be glycosylated by covalent attachment of a sugar (glycan) moiety at hydrophobic surface 1. Preferably, the glycosylation site is an N-glycosylation site comprising an N-X-S/T/C motif, wherein X is any amino acid residue (but preferably, not proline, since proline may reduce glycosylation efficiency). Such glycosylation site may be created, e.g., by substituting a residue with an N, or by inserting an N residue.

Second, a glycosylation site can be introduced (i) in a broader hydrophobic surface, referred herein as "hydrophobic surface 2" (which comprises amino acid residues 145-167 and 230-252), or (ii) at a residue that is within 20 angstroms from one of the two highly hydrophobic fusion loops: fusion loop 1 (FL1) (amino acid residues 155-157), or fusion loop 2 (FL2) (amino acid residues 240-242), or both. For example, based on the crystal structure, it was discovered that the C-terminal region of the ectodomain is in conformational proximity to the highly hydrophobic FL1 or FL2. For example, residues 696-698 (Y, E, and E, respectively, in Merlin strain gB) are believed be within 20 angstroms from FL1 and/or FL2. Therefore, introducing a glycan moiety at the C-terminal region of the ectodomain (e.g., creating a glycosylation site at residues 696-698, e.g., by replace a residue with N, or by inserting an N-X-S/T/C sequence) can also create a physical barrier to reduce aggregation and/or adhesion of the monomeric trimers.

Third, a mutation can be introduced in hydrophobic surface 1 (which comprises residues 154-160 and 236-243), wherein the mutation results in a reduction of overall hydrophobicity index of said hydrophobic surface 1. Creating a more hydrophilic surface can reduce aggregation and/or adhesion of the monomeric trimers.

Fourth, because the C-terminal region of the ectodomain is in conformational proximity to hydrophobic surface 1, a heterologous sequence can be added to the C-terminal region of the ectodomain to "mask" the hydrophobic surface. It is believed that the heterologous sequence can serve as a lipid to cover the hydrophobic surface, thereby reducing aggregation and/or adhesion of the monomeric trimers. Preferably, the heterologous sequence comprises an amphipathic peptide. An amphipathic peptide comprises a hydrophobic portion that can interact with the hydrophobic surface of the monomeric trimer, and the peptide also comprises a hydrophilic surface that can be exposed to aqueous solution.

These four types of mutations can be used singularly, or in any combination, to produce a recombinant gB protein. For example, the gB can comprise two mutations, one creating a glycosylation site in said hydrophobic surface 1 or hydrophobic surface 2, and the other replacing a hydrophobic residue with a more hydrophilic residue.

Accordingly, the invention provides modified gB proteins and immunogenic fragments thereof comprising a glycosylation site and/or one or more mutations that reduce aggregation and/or adhesion of the monomeric gB trimers.

In general, gB proteins and immunogenic fragments described herein does not comprise a transmembrane (TM) domain (i.e., the TM domain of gB is deleted).

2. Definitions gB is an envelope glycoprotein B having numerous roles, one of which is the involvement in the fusion of the cytomegalovirus with host cells. It is encoded by the UL55 gene of HCMV genome. The size of the native form of gB depends on the size of the open reading frame (ORF) which may vary a little according to the strain. For example, the ORF of AD169 strain, which is 2717 bp long, encodes a full length gB of 906 amino acids, whereas the ORF of Towne strain encodes a full length gB of 907 amino acids. Although the present invention is applicable to gB proteins originating from any CMV strain, in order to facilitate its understanding, when referring to amino acid positions in the present specification, the numbering is given in relation to the amino acid sequence of the gB protein of SEQ ID NO:1 originating from the clinical isolate Merlin strain, unless otherwise stated. The present invention is not, however, limited to the Merlin strain. Comparable amino acid positions in a gB protein of any other CMV strains can be determined by those of ordinary skill in the art by aligning the amino acid sequences using readily available and well-known alignment algorithms (such as BLAST, using default settings; ClustalW2, using default settings; or algorithm disclosed by Corpet, Nucleic Acids Research, 1998, 16(22):10881-10890, using default parameters). Accordingly, when referring to a "CMV gB protein", it is to be understood as a CMV gB protein from any strain (in addition to Merlin strain). The actual number may have to be adjusted for gB proteins from other strains depending on the actual sequence alignment.

For example, fusion loop 1 (FL1) is defined as consisting of amino acid residues 155-157, and fusion loop 2 (FL2) is defined as consisting of amino acid residues 240-242. These numbers are in relation to the amino acid sequence of the gB protein of SEQ ID NO: 1. FL1 and FL2 sequences/positions from gB proteins of other CMV strains, or other gB mutants or variants, or fragments of gB can be ascertained using standard sequence alignment programs that align a query sequence with SEQ ID NO: 1, and identifies residues that matches with 155-157 and 240-242 of SEQ ID NO: 1.

Specific amino acid residue positions are also numbered according to SEQ ID NO: 1. For example, "Y160" refers to position 160 of SEQ ID NO: 1 (which is a Y), as well as corresponding residues from other gB sequences (or variants or fragments) that match with Y160 of SEQ ID NO: 1, when the sequence is aligned with SEQ ID NO: 1. For simplicity, any residue from a gB sequence (or variant or fragment) that corresponds to Y160 of SEQ ID NO: 1 is referred to as Y160, although the actual position of that residue may or may not be 160, and the actual residue may or may not be Y. For example, a conservative substitution (e.g., F) may be aligned with Y160 of SEQ ID NO: 1. A conservative substitution is typically identified as "positive" or "+" by BLAST 2.

Similarly, mutations are also identified according to the numbering of SEQ ID NO: 1. For example, Y160T means that any residue from a gB sequence (or variant or fragment) that corresponds to Y160 of SEQ ID NO: 1 is mutated to T.

An amino acid residue of a query sequence "corresponds to" a designated position of a reference sequence (e.g., Y160 of SEQ ID NO: 1) when, by aligning the query amino acid sequence with the reference sequence, the position of the residue matches the designated position. Such alignments can be done by hand or by using well-known sequence alignment programs such as ClustalW2, or "BLAST 2 Sequences" using default parameters.

Figure 1:
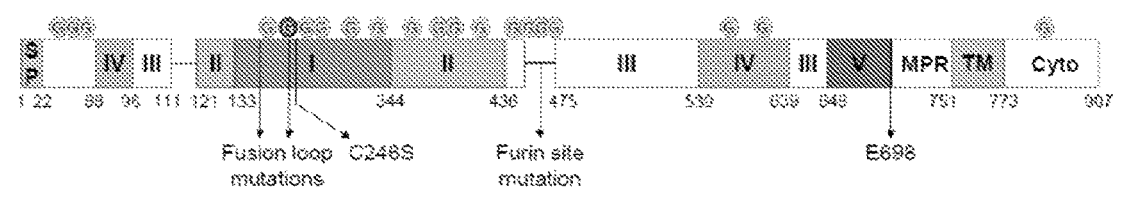

The native form of Merlin gB contains in the N-terminal to C-terminal direction of the protein (see FIG. 1) (i) a signal peptide, known to be involved in the polypeptide intracellular trafficking including targeting the polypeptide towards secretion, followed by (ii) a region called the leader sequence, (iii) an extracellular domain which also comprises an endoproteolytic cleavage site of a furin type between amino acid residues 456 and 460, (iv) a transmembrane domain and (v) a C-terminal cytoplasmic domain. The ectodomain comprises two hydrophobic fusion loops: fusion loop 1 (FL1) (amino acid residues 155-157) or fusion loop 2 (FL2) (amino acid residues 240-242).

"Hydrophobic surface 1" consists of amino acid residues 154-160 and 236-243. "Hydrophobic surface 2" consists of amino acid residues 145-167 and 230-252. Again, amino acid residues are identified by the position according to the gB protein from the Merlin strain (SEQ ID NO:1). Corresponding amino acid residues from other gB sequences or fragments can be ascertained by aligning the query sequence against SEQ ID NO: 1.

CMV gB ectodomain refers to a CMV gB fragment that comprises substantially the extracellular portion of mature CMV gB protein, with or without the signal peptide, and lacks the transmembrane domain and C-terminal domain of naturally occurring CMV gB protein. In a preferred embodiment, the ectodomain comprises amino acid residues 69 to 698.

The transmembrane (TM) domain refers to the region that spans the cell membrane. The minimal region consists of amino acid residues 750-766.

A monomeric trimer is formed by three gB proteins (also referred to as subunits). A dimeric trimer is formed by dimerization of two monomeric trimmers. Thus, a dimeric trimer comprises six gB subunits.

An immunogenic fragment of gB refers to a fragment that retains at least one predominant immunogenic epitope of the full-length gB. Several antigenic domains (AD) of gB have been described. See, e.g., Wiegers et al., J Virol. 2014 Oct. 15. pii: JVI.02393-14; Epub ahead of print; Potzsch et al., PLoS Pathog 7(8): e1002172. doi:10.1371/journal.ppat.1002172 (August 2011); Spindler et al., J Virol. 2013 August; 87(16):8927-39. doi: 10.1128/JVI.00434-13; Ohlin et al., J. Virol. 67(2): 703-710, 1993.

AD-1 is approximately 80 residues between positions 560 and 640 of gB of strain AD169. It is the immunodominant region of gB since nearly all sera from HCMV-infected individuals recognize AD-1. AD-2, located at the extreme amino terminus of the protein, comprises at least two distinct sites between a.a. 50 and 78 of gB of AD169. Site I (a.a. 50-54 of AD169) differs between strains and is recognized by strain specific antibodies some of which neutralize in a complement-dependent manner. Site II (a.a. 69-78 of AD169) is common to all HCMV strains and induces broadly neutralizing antibodies. An additional linear a.a. sequence, AD-3 (a.a. 783-906), recognized by gB-specific antibodies in human sera, includes epitopes at the intraluminal/intraviral part of the molecule. AD-4 is formed by a discontinuous sequence comprising amino acids 121 to 132 and 344 to 438 of gB of strain AD169. AD-5 is formed by a continuous sequence comprising a.a. 133-343 of strain AD169. In preferred embodiments, the immunogenic fragment described herein comprises an antigenic domain selected from the group consisting of AD-1, AD-2, AD-3, AD-4, AD-5, and a combination thereof.

A heterologous sequence refers to an amino acid or nucleotide sequence that is not found in naturally occurring CMV gB protein, or a nucleic acid encoding a CMV gB protein.

An amphipathic peptide refers to peptides containing both hydrophilic and hydrophobic amino acid residues, where spatial separation of these residues, such as for example through the secondary structure of the peptide, result in their ability to partition at an interface between a polar and a non-polar medium such as a lipidic interface, an air/water interface, hydrophilic solvent/hydrophobic solvent interface and air/packaging material interface. Typically, amphipathic peptides present an amphipathicity defined by a mean hydrophobic moment between about 0 and about 0.9, according to the Eisenberg plot (Eisenberg et al., J. Mol. Biol. 179:125-142, 1984).

3. Recombinant GB Proteins

CMV gB protein comprises an N-terminal extracellular domain of approximately 725 amino acids, followed by a transmembrane region and a C-terminal domain. Most known neutralizing epitopes on gB map to the ectodomain of gB, as do two hydrophobic regions, referred to as fusion loops 1 (FL1) and 2 (FL2). It is believed that gB inserts these fusion loops into the target cellular membrane and, by means of a conformational change in its structure, brings the viral and cellular membrane in juxtaposition to facilitate viral/cell membrane fusion.

As disclosed herein, the inventors solved the crystal structure of the CMV gB, in monomeric trimer form, complexed with an anti-gB antibody (Fab fragment). Based on the crystal structure, the inventors identified an exposed hydrophobic surface that can cause aggregation of monomeric gB trimers (e.g., formation of dimeric trimers, which comprise six gB subunits), as well as undesired adhesion of monomeric trimer to the host cell (e.g., to cell membrane, ER membrane, other hydrophobic proteins, aggregated proteins, etc.). A narrower hydrophobic surface (hydrophobic surface 1) consists of residues 154-160 and 236-243. A broader hydrophobic surface (hydrophobic surface 2) consists of residues 145-167 and 230-252.

Based on this information, the inventors identified several categories of mutations that can reduce the aggregation between the monomeric trimers, and/or adhesion of the monomeric trimer to the host cell (e.g., to cell membrane, ER membrane, other hydrophobic proteins, aggregated proteins, etc.). In particular, the mutations in general allow the monomeric trimer to be secreted from a host cell (e.g., when expressed heterologously in mammalian cells), thereby significantly improving the efficiency of production process.

In particular, four strategies have been identified. First is to introduce a glycosylation site within hydrophobic surface 1 (residues 154-160 and 236-243). Second is to introduce a glycosylation site in either hydrophobic surface 2 (residues 145-167 and 230-252), and/or at a residue that is within 20 angstroms from fusion loop 1 (FL1) (residues 155-157) and/or fusion loop 2 (FL2) (residues 240-242). For example, residues 696, 697, and 698 are located within 20 angstroms from FL1 and/or FL2 and can be used to introduce a glycosylation site. Third is to reduce the overall hydrophobicity index of the hydrophobic surface 1 or 2. The fourth is to include a heterologous sequence at the C-terminal region of the ectodomain to at least partially mask the hydrophobic surface 1 or 2.

These mutations can be used individually and in combination to overcome the hydrophobicity of the exposed hydrophobic surface. For example, mutants can be assessed by size exclusion chromatography and potentially through electron microscopy to verify the formation of soluble, monomeric trimers of gB.

In general, the recombinant human CMV gB protein (or immunogenic fragment thereof) described herein does not comprise a transmembrane (TM) domain. The TM domain minimally consists of amino acid residues 750-766. However, because residues adjacent to this minimal TM region are generally hydrophobic, in some preferred embodiments, the gB protein (or immunogenic fragment thereof) does not comprise (i) amino acid residues 700-766, (ii) amino acid residues 700-776, (iii) amino acid residues 698-766, or (iv) amino acid residues 698-776. Deletion of these amino acid residues are believe to facilitate the recombinant production of gB proteins disclosed herein. Alternatively, in certain embodiments, the gB protein (or immunogenic fragment thereof) does not comprise two stretches of hydrophobic residues, first being residues 725 to 744, and the second being 751 to 773.

The gB proteins of the invention can be gB variants that have various degrees of identity to SEQ ID NO: 1 such as at least 60%, 70%, 80%, 85%, 90%, 91%, 92%, 93%, 94%, 95%, 96%, 97%, 98% or 99% identical to the sequence recited in SEQ ID NO: 1. In certain embodiments, the gB variant proteins: (i) do not form substantial amount of dimeric trimer; (ii) comprise at least one epitope from SEQ ID NO: 1; and/or (iii) can elicit antibodies (preferably neutralizing antibodies) in vivo which immunologically cross react with a CMV virion. Substantial amount of dimeric trimer means that, e.g., at least 35%, at least 30%, at least 25%, at least 20%, at least 15%, at least 10%, or at least 5%, of the total gB subunits are in dimeric trimer form.

A. Glycosylation

In one aspect, disclosed herein are gB proteins, or immunogenic fragments thereof, that comprise a glycosylation site within hydrophobic surface 1. In particular, the invention provides a cytomegalovirus (CMV) gB protein, or an immunogenic fragment thereof, wherein (i) said gB protein, or immunogenic fragment thereof, does not comprise a transmembrane (TM) domain; and (ii) said gB protein, or immunogenic fragment thereof, comprises a mutation that results in a glycosylation site within hydrophobic surface 1. Preferably, said glycosylation site is an N-glycosylation site comprising N-X-S/T/C motif, wherein X is any amino acid residue (preferably not proline). More preferably, said glycosylation site is an N-glycosylation site comprising N-X-S/T motif, wherein X is any amino acid residue (preferably not proline). Accordingly, when recombinantly produced in a suitable host cell (e.g., a host cell that comprises a glycosylation enzyme), the gB protein or immunogenic fragment thereof comprises a glycan moiety attached to a residue within hydrophobic surface 1.

In another aspect, disclosed herein are gB proteins, or immunogenic fragments thereof, that comprise a glycosylation site within hydrophobic surface 2, or at a residue that is in conformational proximity to FL1 and/or FL2. In particular, the invention provides a recombinant cytomegalovirus (CMV) gB protein, or an immunogenic fragment thereof, wherein (i) said gB protein, or immunogenic fragment thereof, does not comprise a transmembrane (TM) domain; and (ii) said gB protein, or immunogenic fragment thereof, comprises a mutation that results in a glycosylation site, wherein said glycosylation site is (1) within hydrophobic surface 2 (amino acid residues 145-167 and 230-252); or (2) at a residue that is within 20 angstroms from fusion loop 1 (FL1) (amino acid residues 155-157) and/or fusion loop 2 (FL2) (amino acid residues 240-242). Accordingly, when recombinantly produced in a suitable host cell (e.g., a host cell that comprises a glycosylation enzyme), the gB protein or immunogenic fragment thereof comprises a glycan moiety attached to a residue within hydrophobic surface 2, or a residue that is within 20 angstroms from fusion loop 1 (FL1) and/or fusion loop 2 (FL2).

As disclosed herein, attachment of a glycan creates a physical barrier (as well as a more hydrophilic surface) to reduce aggregation/adhesion via the hydrophobic surface. The glycosylation site can be within the narrower hydrophobic surface 1 or broader hydrophobic surface 2 disclosed herein. Alternatively, the glycosylation site can be at residue that is in conformational proximity to the highly hydrophobic FL1, and/or FL2 (e.g., within 30 angstroms, or within 25 angstroms, or within 20 angstroms, or within 15 angstroms, or within 14 angstroms, or within 13 angstroms, or within 12 angstroms, or within 11 angstroms, or within 10 angstroms, or within 9 angstroms, or within 8 angstroms, or within 7 angstroms, or within 6 angstroms, or within 5 angstroms, from one of the atoms from the FL1 and/or FL2). For example, based on the crystal structure, the C-terminal region of the ectodomain is in conformational proximity to FL1 and/or FL2. For example, residues 696, 697, and 698 are all located within 20 angstroms from FL1 and/or FL2 and can be used to introduce a glycosylation site.

Glycosylation sites can be introduced into desired locations by suitable modification of amino acid sequences of the gB protein. Preferably, N-linked glycosylation sites, comprising the N-X-S/T/C motif, are introduced. Preferably, the motif is N-X-S/T. Preferably, X is not proline.

For example, N-linked glycosylation can be introduced in the hydrophobic surface by changing the amino acid sequence of the gB protein to include the N-X-S/T/C motif for N-linked glycosylation. This can be achieved by inserting the N-X-S/T/C motif into the gB sequence, or by replacing one or more amino acids to produce the glycosylation site, or any combination of addition and mutation resulting in the N-X-S/T/C motif. For example, N may be added, while position S/T/C may be mutated; or N may be mutated from another residue, while position S/T/C is added. When the protein is expressed in suitable cells, for example, mammalian cells, N-linked glycans will be attached to the N-residue to create an N-glycosylated gB.

Similarly, sites for O-linked glycosylation can also be added. In O-linked glycosylation, the carbohydrate moiety is linked to the hydroxyl oxygen of serine and threonine. In addition, 0-linked glycosylation also occurs at tyrosine, 5-hydroxylysine, and 4-hydroxyproline.

In certain embodiments, the mutation comprises an insertion of N-X-S/T/C sequence, (such as N-X-S, N-X-T, N-X-C, N-G-S, N-G-T, N-A-S, N-A-T, etc., where X is any amino acid, but preferably not proline). In certain embodiments, the mutation comprises an insertion of N-X-S/T/C sequence (such as N-X-S, N-X-T, N-X-C, N-G-S, N-G-T, N-A-S, N-A-T, etc., where X is any amino acid, but preferably not proline) in fusion loop 1 (FL1) (amino acid residues 155-157), fusion loop 2 (FL2) (amino acid residues 240-242), or both. In certain embodiments, the mutation comprises an insertion of N-X-S/T/C sequence (such as N-X-S, N-X-T, N-X-C, N-G-S, N-G-T, N-A-S, N-A-T, etc., where X is any amino acid, but preferably not proline) without mutating other residues in FL1 and FL2.

In certain embodiments, the mutation comprises mutating $^{236}$RGSTW (SEQ ID NO: 12) to $^{236}$RGSTNGTW (SEQ ID NO: 13); $^{240}$WLYR (SEQ ID NO: 14) to $^{240}$WLYNGTR (SEQ ID NO: 15), or a combination thereof.

In certain embodiments, the gB protein or immunogenic fragment thereof comprises a mutation that is selected from the group consisting of (i) R236N, (ii) G237N, (iii) T158N, (iv) W240N and Y242T, (v) W240N and Y242S, (vi) W240N and Y242C, and a combination thereof. In certain embodiments, the gB protein or immunogenic fragment thereof comprises a mutation that is selected from the group consisting of (i) R236N, (ii) G237N, (iii) T158N, and a combination thereof. In certain embodiments, the mutation comprises T158N mutation.

In certain embodiments, the mutation comprises (i) W240N; and (ii) Y242T, Y242S, or Y242C mutations. The combination of the two mutations creates a glycosylation site.

In addition to glycosylation, the gB protein and immunogenic fragments thereof described herein can also comprises one or more mutations that reduce the overall hydrophobicity index of the hydrophobic surface, as described below, and/or comprises a C-terminal heterologous sequence, as described below.

B. Reducing Overall Hydrophobicity Index

In another aspect, the invention provides a recombinant cytomegalovirus (CMV) gB protein, or an immunogenic fragment thereof, wherein (i) said gB protein, or immunogenic fragment thereof, does not comprise a transmembrane (TM) domain; and (ii) said gB protein, or immunogenic fragment thereof, comprises a mutation in hydrophobic surface 1 (amino acid residues 154-160 and 236-243), or hydrophobic surface 2 (amino acid residues 145-167 and 230-252); wherein said mutation results in a reduction of overall hydrophobicity index of said hydrophobic surface 1 or 2.

In preferred embodiments, the mutation is not a deletion or substitution of an amino acid in fusion loop 1 (FL1) (amino acid residues 155-157) and fusion loop 2 (FL2) (amino acid residues 240-242). Thus, in certain embodiments, gB proteins comprising a deletion or substitution of an amino acid residue selected from the group consisting of amino acid residues 155, 156, 157, 240, 241 and 242 are excluded.

The hydrophobicity of a particular amino acid sequence can be determined using a hydrophobicity scale, such as the Kyte and Dolittle scale (Kyte et al. 1982. J. Mol. Bio. 157: 105-132). Hydrophobicity of an amino acid sequence or a fragment thereof is dictated by the type of amino acids composing this sequence or a fragment thereof. Amino acids are commonly classified into distinct groups according to their side chains. For example, some side chains are considered non-polar, i.e. hydrophobic, while some others are considered polar. In the sense of the present invention, alanine (A), glycine (G), valine (V), leucine (L), isoleucine (I), methionine (M), proline (P), phenylalanine (F) and tryptophan (W) are considered to be part of hydrophobic amino acids, while serine (S), threonine (T), asparagine (N), glutamine (Q), tyrosine (Y), cysteine (C), lysine (K), arginine (R), histidine (H), aspartic acid (D) and glutamic acid (E) are considered to be part of polar amino acids. Regardless of their hydrophobicity, amino acids are also classified into subgroups based on common properties shared by their side chains. For example, phenylalanine, tryptophan and tyrosine are jointly classified as aromatic amino acids and will be considered as aromatic amino acids within the meaning of the present invention. Aspartate (D) and glutamate (E) are part of the acidic or negatively charged amino acids, while lysine (K), arginine (R) and histidine (H) are part of the basic or positively charged amino acids, and they will be considered as such in the sense of the present invention. Hydrophobicity scales are available which utilize the hydrophobic and hydrophilic properties of each of the 20 amino acids and allocate a hydrophobic score to each amino acid, creating thus a hydrophobicity ranking.

As an illustrative example only, the Kyte and Dolittle scale may be used (Kyte et al. 1982. J. Mol. Bio. 157: 105-132). This scale allows one skilled in the art to calculate the average hydrophobicity within a segment of predetermined length. Accordingly, hydrophobic regions in an amino acid sequence may be identified by the skilled person as potential targets for mutation in accordance with the present invention. The ability of the mutation of said regions to induce an improved product profile of the resulting mutant protein, i.e. favoring the monomeric trimers proportion within the population, may then be tested as described below. The mutation of a hydrophobic region may be in an addition, deletion, or substitution of the amino acid within the hydrophobic surface (e.g., substituting hydrophobic amino acids with polar amino acids).

Whether a mutation can reduce the overall hydrophobicity index of the hydrophobic surface can also be determined, for example, by analyzing the resulting effect of said mutation on the product profile. For example, upon recombinant expression in host cells, a mutation should result in an improved, monomeric trimer-enriched profile (e.g., at least 50%, at least 55%, at least 60%, at least 65%, at least 70%, at least 75%, at least 80%, at least 85%, at least 90%, or at least 95%, of the recombinantly produced gB (or an immunogenic fragment thereof) is in monomeric trimer form.

In certain embodiments, the mutation comprises replacing a hydrophobic amino acid residue within hydrophobic surface 1 or 2 with an amino acid residue that comprises a charged side chain or a polar side chain. In certain embodiments, the hydrophobic amino acid residue is selected from the group consisting of: A, V, L, I, P, M, F, G, and W. In certain embodiments, the amino acid residue comprising a charged side chain is selected from the group consisting of D, E, K, R, and H. In certain embodiments, the amino acid residue comprising a polar side chain is selected from the group consisting of S, T, C, N, Q, and Y.

In certain embodiments, the mutation comprises deleting a hydrophobic amino acid residue within hydrophobic surface 1 or 2. In certain embodiments, the hydrophobic amino acid residue is selected from the group consisting of: A, V, L, I, P, M, F, G, and W.

In certain embodiments, the mutation comprises inserting an amino acid residue that comprises a charged side chain or a polar side chain in hydrophobic surface 1 or 2. In certain embodiments, the hydrophobic amino acid residue is selected from the group consisting of: A, V, L, I, P, M, F, G, and W. In certain embodiments, the amino acid residue comprising a charged side chain is selected from the group consisting of D, E, K, R, and H. In certain embodiments, the amino acid residue comprising a polar side chain is selected from the group consisting of S, T, C, N, Q, and Y.

In certain embodiments, the mutation comprises replacing Y160 with an amino acid residue that comprises a charged side chain or a polar side chain.

In certain embodiments, the amino acid residue comprising a charged side chain is selected from the group consisting of D, E, K, R, and H. In certain embodiments, the gB protein or immunogenic fragment thereof comprises a Y160E mutation.

In certain embodiments, the amino acid residue comprising a polar side chain is selected from the group consisting of S, T, C, N, and Q. In certain embodiments, the gB protein or immunogenic fragment thereof comprises a Y160T mutation.

In certain embodiments, the gB protein or immunogenic fragment thereof comprises $^{158}TTY^{160}$ to $^{158}NTT^{160}$ mutation.

In certain embodiments, the mutation comprises replacing S238 with an amino acid residue that comprises a charged side chain.

In certain embodiments, the amino acid residue comprising a charged side chain is selected from the group consisting of D, E, K, R, and H. In certain embodiments, the gB protein or immunogenic fragment thereof comprises a S238E mutation.

In certain embodiments, the mutation comprises replacing T239 with an amino acid residue that comprises a charged side chain.

In certain embodiments, the amino acid residue comprising a charged side chain is selected from the group consisting of D, E, K, R, and H. In certain embodiments, the gB protein or immunogenic fragment thereof comprises a T239E mutation.

In certain embodiments, the gB protein or immunogenic fragment thereof comprises a S238E mutation and a T239E mutation.

In certain embodiments, the gB protein or immunogenic fragment thereof comprises an R236E mutation or R236D mutation. In certain embodiments, the gB protein or immunogenic fragment thereof comprises an R236E mutation.

In certain embodiments, the gB protein or immunogenic fragment thereof comprises mutations selected from the group consisting of: (i) R236E and S238E; (ii) R236E and T239E; and (iii) R236E. S238E, and T239E.

In certain embodiments, the gB protein or immunogenic fragment thereof comprises a mutation at I156, H157, or a combination thereof to reduce hydrophobicity. In certain embodiments, the residue is replaced with a corresponding residue from gB from another herpes virus species, such as gB from HSV-1, HSV-2, or VZV. In an exemplary embodiment, the gB protein or immunogenic fragment thereof comprises a I156H mutation. In another exemplary embodiment, the gB protein or immunogenic fragment thereof comprises a Y242T mutation.

C. C-Terminal Heterologous Sequence

In another aspect, the invention provides a cytomegalovirus (CMV) gB protein, or an immunogenic fragment thereof, wherein (i) said gB protein, or immunogenic fragment thereof, does not comprise a transmembrane (TM) domain; (ii) said gB protein, or immunogenic fragment thereof, comprises an ectodomain (amino acid residues 69-698); and (iii) said gB protein, or immunogenic fragment thereof, comprises a heterologous sequence that is at least 12 residues long at the C-terminus. In some aspects, the gB protein may be a fusion protein wherein the heterologous sequence is fused at the C-terminus of the ectodomain. In some aspects, the heterologous sequence may be an amphipathic peptide.

The inventors discovered from the crystal structure that the C-terminal region of the ectodomain is in the vicinity of the hydrophobic surface. Further, when the TM domain of gB is deleted, and the cytoplasmic domain is fused directly to the extracellular domain, it was found that the gB protein can form soluble monomeric trimer. It is believed that additional amino acid residues at the C-terminal region can serve as a physical block to at least partially cover or mask the exposed hydrophobic surface, thereby reducing aggregation and/or adhesion of the monomeric trimers.

Preferably, the heterologous sequence is at least about 9, 10, 11, 12, 13, 14, 15, 16, 17, 18, 19, 20, 21, 22, 23, 24, 25, or 30 amino acids long. Preferably, the heterologous sequence will be at least 12 amino acid amino acids long. In a preferred embodiment, the heterologous sequence is about 20 amino acids long. In certain embodiment, the heterologous sequence is no more than about 50, 45, 40, 35, 30, or 25 amino acids long.

Preferably, the heterologous sequence comprises an amphipathic peptide. An amphipathic peptide comprises a hydrophobic portion that can interact with the hydrophobic surface of the monomeric trimer, and the peptide also comprises a hydrophilic surface that can be exposed to aqueous solution.

Examples of amphipathic peptides can be found, e.g., sequences derived from apolipoproteins. Apolipoproteins are lipid-binding proteins that are divided into six major classes (A, B, C, D, E and H) and several sub-classes. The design and synthesis of amphipathic peptides that mimic the properties of apolipoproteins are known, see, e.g., Mishra et al. Biochemistry 1996, Aug. 27; 35(34):11210-20. Specific examples of amphipathic peptides include, e.g., DWLKA-FYDKVAEKLKEAFLA (SEQ ID NO. 3); ELLEKWKEA-LAALAEKLK (SEQ ID NO. 4); FWLKAFYDK-VAEKLKEAF (SEQ ID NO. 5); DWLKAFYDKVAEKLKEAFRLTRKRGLKLA (SEQ ID NO. 6), and DWLKAFYDKVAEKLKEAF (SEQ ID NO. 7).

The mutation strategies described herein can be used singularly or in any combination, such as (i) introducing a glycosylation site and reducing the overall hydrophobicity index of the hydrophobic surface; (ii) introducing a glycosylation site and introducing C-terminal heterologous sequence; (iii) reducing the overall hydrophobicity index of the hydrophobic surface and introducing C-terminal heterologous sequence; and (iv) introducing a glycosylation site, reducing the overall hydrophobicity index of the hydrophobic surface, and introducing C-terminal heterologous sequence.

Specific mutations disclosed herein include:
$^{236}$RGSTW$^{240}$ (SEQ ID NO: 12) mutated to $^{236}$NGSTW$^{240}$ (SEQ ID NO: 16);
$^{236}$RGSTW$^{240}$ (SEQ ID NO: 12) mutated to $^{236}$RNSTW$^{240}$ (SEQ ID NO: 17);
$^{236}$RGSTW$^{240}$ (SEQ ID NO: 12) mutated to $^{236}$EGETW$^{240}$ (SEQ ID NO: 18);
$^{236}$RGSTW$^{240}$ (SEQ ID NO: 12) mutated to $^{236}$EGEEW$^{240}$ (SEQ ID NO: 19).
$^{236}$RGSTW$^{240}$ (SEQ ID NO: 12) mutated to $^{236}$RGSTNGTW$^{243}$ (SEQ ID NO: 13);
$^{240}$WLYR$^{243}$ (SEQ ID NO: 14) mutated to $^{240}$WLYN-GTR$^{246}$ (SEQ ID NO: 15);
$^{158}$TTY$^{160}$ mutated to $^{158}$NTT$^{160}$;
$^{158}$TTY$^{160}$ mutated to $^{158}$TTE$^{160}$; and
$^{156}$IH$^{157}$ and $^{240}$WLY$^{242}$ mutated to $^{156}$HR$^{157}$ and $^{240}$NLT$^{242}$.

The mutations relating to glycosylation sites and hydrophobicity are not limited to the above-described mutations. Further mutations not described herein, as well as combinations of mutations described herein, may be performed. The resulting mutants can be analyzed, e.g., by scanning electron microscope (SEM), computer modeling, sedimentation (such as analytical ultracentrifugation (AUC)), chromatography etc, to assess the production of monomeric trimer. For example, size exclusion chromatography (SEC), such as size exclusion chromatography based on UV (SEC-UV) may be used. Alternatively, the sample can be treated with a cross-linking agent, so as to form covalent bonds between two proteins. After cross-linking, loading the sample on a gel in denaturing conditions, such as SDS-PAGE, and staining the gel for the presence of proteins, for example with Coomassie blue or silver nitrate, will display aggregates, if any, which are separated according to their molecular weight. For instance, the CMV AD169 gB (with transmembrane domain deleted) has an expected molecular weight of 92 kDa. If forming a monomeric trimer, the expected average molecular weight should be about 276 kDa.

D. Other Modifications

Other modifications may also be introduced to facilitate the recombinant production of gB protein, or immunogenic fragments thereof.

In general, the original C-terminal cytoplasmic domain of the gB protein can be deleted to a varying extent. In certain embodiments, at least 10%, at least 20%, at least 30%, at least 40%, at least 50%, at least 60%, at least 70%, more suitably 80%, at least 90%, or 100% of the amino acids of the cytoplasmic domain is deleted.

In certain embodiments, the recombinant human CMV gB protein (or immunogenic fragment thereof) comprises a furin cleavage site mutation. The ectodomain comprises a furin cleavage site at residues 457-460 (RTKR (SEQ ID NO: 20) for Merlin strain; SEQ ID NO: 1). Such mutation can be, for example, R457S, R460S, or R457S/R460S double mutations. Such mutation(s) can destroy the furin cleavage site, thereby promoting the production of an intact gB or gB immunogenic fragment (e.g., the ectodomain). There is another potential furin cleavage site at residues 774-777 (RQRR) (SEQ ID NO: 21), which may also be mutated if present in the gB protein or immunogenic fragment described herein.

In certain embodiments, the recombinant human CMV gB protein (or immunogenic fragment thereof) comprises a mutation at C246. Such mutation can be, e.g., C246S, C246A, or C246G. It appears that C246 is an unpaired cysteine, and mutating this unpaired cysteine can reduce the undesired formation of inter-molecular disulfide bonds. There is another potential unpaired Cysteine at the C-terminal region (residue 779). If present, this cysteine may also be mutated.

Optionally, to facilitate expression and recovery, the gB protein (or immunogenic fragment thereof) may include a signal peptide at the N-terminus. A signal peptide can be selected from among numerous signal peptides known in the art, and is typically chosen to facilitate production and processing in a system selected for recombinant expression of the gB protein (or immunogenic fragment thereof). In general, signal peptides are 5-30 amino acids long, and are typically present at the N-terminus of a newly synthesized protein. The core of the signal peptide generally contains a long stretch of hydrophobic amino acids that has a tendency to form a single alpha-helix. In addition, many signal peptides begin with a short hydrophilic (usually positively charged) stretch of amino acids, which may help to enforce proper topology of the polypeptide during translocation. At the end of the signal peptide (C-terminus), there is typically a stretch of hydrophilic amino acids that is recognized and cleaved by signal peptidase. Signal peptidase may cleave either during or after completion of translocation to generate a free signal peptide and a mature protein.

In certain embodiments, the signal peptide is the one naturally present in the native gB proteins. For Merlin and AD169 strains, the signal peptide is located at residues 1-22 of SEQ ID NO:1 and SEQ ID NO: 2, respectively. Signal peptide from other strains can be identified by sequence alignment. Alternatively, the signal peptide may be a heterologous sequence in that the sequence arises from a protein distinct from gB. Exemplary signal peptides suitable for use in the context of the gB protein (or immunogenic fragment thereof) described herein include signal peptides of tissue plasminogen activator (tPA), Herpes Simplex Virus (HSV) gD protein, human endostatin, HIV gp120, CD33, human Her2Neu, gp67, or Epstein Barr Virus (EBV) gp350. The signal peptide can be non-native and may comprise mutations, such as substitutions, insertions, or deletions of amino acids. In particular, mutations can be introduced at C-terminal part of the signal peptide.

Optionally, the CMV gB proteins (or immunogenic fragment thereof) of the invention can include the addition of an amino acid sequence that constitutes a tag, which can facilitate detection (e.g. an epitope tag for detection by monoclonal antibodies) and/or purification (e.g. a polyhistidine-tag to allow purification on a nickel-chelating resin) of the proteins. Examples of affinity-purification tags include, e.g., His tag (hexahistidine (SEQ ID NO: 8), binds to metal ion), maltose-binding protein (MBP) (binds to amylose), glutathione-S-transferase (GST) (binds to glutathione), FLAG tag (Asp-Tyr-Lys-Asp-Asp-Asp-Asp-Lys (SEQ ID NO: 9), binds to an anti-flag antibody), Strep tag (Ala-Trp-Arg-His-Pro-Gln-Phe-Gly-Gly (SEQ ID NO: 10), or Trp-Ser-His-Pro-Gln-Phe-Glu-Lys (SEQ ID NO: 11), binds to streptavidin or a derivative thereof), HA tag, MYC tag, or combination thereof.

In a certain embodiment, cleavable linkers may be used. This allows for the tag to be separated from the purified complex, for example by the addition of an agent capable of cleaving the linker. A number of different cleavable linkers are known to those of skill in the art. Such linkers may be cleaved for example, by irradiation of a photolabile bond or acid-catalyzed hydrolysis. There are also polypeptide linkers which incorporate a protease recognition site and which can be cleaved by the addition of a suitable protease enzyme.

In other embodiments, it may be more desirable to express gB (or immunogenic fragment thereof) without an exogenous tag sequence, for example, for clinical safety or efficacy reasons.

The recombinant CMV gB protein (or immunogenic fragment thereof) disclosed herein may also contain a trimerization tag to improve trimerization. For example, a T4 fibritin foldon tag or a GCN4 trimerization domain may be inserted at the C-terminus of the CMV gB protein (or immunogenic fragment thereof).

Also provided herein is a CMV complex comprising the recombinant gB protein (or immunogenic fragment thereof) described herein. In certain embodiments, the complex is a monomeric trimer consisting of three gB protein subunits.

In certain embodiments, at least 50%, at least 55%, at least 60%, at least 65%, at least 70%, at least 75%, at least 80%, at least 85%, at least 90%, or at least 95%, of the recombinantly produced gB (or an immunogenic fragment thereof) is in monomeric trimer form. In certain embodiments, no more than 50%, no more than 45%, no more than 40%, no more than 35%, no more than 30%, no more than 25%, no more than 20%, no more than 15%, no more than 10%, no more than 5%, of the recombinantly produced gB (or an immunogenic fragment thereof) is in dimer trimer form.

4. Recombinant Expression of GB

Also provided herein are nucleic acids encoding CMV gB and immunogenic fragments thereof, as described herein. The nucleic acid, such as DNA, may be used for recombinant production of gB protein.

The invention also provides a host cell comprising the nucleic acids described herein. When the host cell is cultured under a suitable condition, the nucleic acids can express a gB protein (or an immunogenic fragment thereof). Preferably, said gB protein (or an immunogenic fragment thereof) forms a monomeric trimer. Preferably, the monomeric trimer can be secreted from the host cell.

Suitable host cells include, for example, insect cells (e.g., *Aedes aegypti, Autographa californica, Bombyx mori, Drosophila melanogaster, Spodoptera frugiperda,* and *Trichoplusia ni*), mammalian cells (e.g., human, non-human primate, horse, cow, sheep, dog, cat, and rodent (e.g., hamster)), avian cells (e.g., chicken, duck, and geese), bacteria (e.g., *E. coli, Bacillus subtilis,* and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), *Tetrahymena* cells (e.g., *Tetrahymena thermophila*) or combinations thereof.

For mutants that comprise a glycosylation site, the host cell should be one that has enzymes that mediate glycosylation. Bacterial hosts are generally not suitable for such mutants, unless the strain is modified to introduce glycosylation enzymes; instead, a eukaryotic host, such as insect cell, avian cell, or mammalian cell should be used.

Suitable insect cell expression systems, such as baculovirus systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. For example, for expression in insect cells a suitable baculovirus expression vector, such as pFastBac (Invitrogen), is used to produce recombinant baculovirus particles. The baculovirus particles are amplified and used to infect insect cells to express recombinant protein. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)).

Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in Vaccine 27:4975-4982 (2009) and WO2005/042728), EB66 cells, and the like.

Preferably, the host cells are mammalian cells (e.g., human, non-human primate, horse, cow, sheep, dog, cat, and rodent (e.g., hamster). Suitable mammalian cells include, for example, Chinese hamster ovary (CHO) cells, human embryonic kidney cells (HEK-293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like.

In certain embodiments, the host cell is a CHO cell. In certain embodiments, the polynucleotide encoding the gB protein (or immunogenic fragment thereof) described herein is stably integrated into the genome of the CHO cell.

Various CHO cell lines are also available from European Collection of Cell Cultures (ECACC), or American Type Culture Collection (ATCC), such as CHO cell lines hCBE11 (ATCC® PTA-3357™), E77.4 (ATCC® PTA-3765™), hLT-B: R-hG1 CHO #14 (ATCC® CRL-11965™), MOR-CHO-MORAb-003-RCB (ATCC® PTA-7552™), AQ.C2 clone 11B (ATCC® PTA-3274™) AQ.C2 clone 11B (ATCC® PTA-3274™), hsAQC2 in CHO-DG44 (ATCC® PTA-3356™), xrs5 (ATCC® CRL-2348™), CHO-K1 (ATCC® CCL-61 ™), Lec [originally named Pro-5WgaRI3C] (ATCC® CRL-1735™), Pro-5 (ATCC® CRL-1781 ™), ACY1-E (ATCC® 65421 ™), ACY1-E (ATCC® 65420™), pgsE-606 (ATCC® CRL-2246™), CHO-CD36 (ATCC® CRL-2092™), pgsC-605 (ATCC® CRL-2245™), MC2/3 (ATCC® CRL-2143™), CHO-ICAM-1 (ATCC® CRL-2093™) and pgsB-618 (ATCC® CRL-2241 ™). Any one of these CHO cell lines may be used.

Other commercially available CHO cell lines include, e.g., FreeStyle™ CHO-S Cells and Flp-In™-CHO Cell Line from Life Technologies.

Methods for expressing recombinant proteins in CHO cells in general have been disclosed. See, e.g., in U.S. Pat. Nos. 4,816,567 and 5,981,214.

In certain embodiments, the recombinant nucleic acids are codon optimized for expression in a selected prokaryotic or eukaryotic host cell.

To facilitate replication and expression, the nucleic acids can be incorporated into a vector, such as a prokaryotic or a eukaryotic expression vector. Exemplary vectors include plasmids that are able to replicate autonomously or to be replicated in a host cell. Typical expression vectors contain suitable promoters, enhancers, and terminators that are useful for regulation of the expression of the coding sequence(s) in the expression construct. The vectors may also comprise selection markers to provide a phenotypic trait for selection of transformed host cells (such as conferring resistance to antibiotics such as ampicillin or neomycin).

Exemplary procedures sufficient to guide one of ordinary skill in the art through the production of recombinant CMV gB nucleic acids can be found in Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2003); and Ausubel et al., Short Protocols in Molecular Biology: A Compendium of Methods from Current Protocols in Molecular Biology, 4th ed., Wiley & Sons, 1999.

Also provided herein is a cell culture comprising the host cell described herein. The cell culture can be large scale, e.g., at least about 10 L, at least about 20 L, at least about 30 L, at least about 40 L, at least about 50 L, at least about 60 L, at least about 70 L, at least about 80 L, at least about 90 L, at least about 100 L, at least about 150 L, at least about 200 L, at least about 250 L, at least about 300 L, at least about 400 L, at least about 500 L, at least about 600 L, at least about 700 L, at least about 800 L, at least about 900 L, at least about 1000 L, at least about 2000 L, at least about 3000 L, at least about 4000 L, at least about 5000 L, at least about 6000 L, at least about 10,000 L, at least about 15,000 L, at least about 20,000 L, at least about 25,000 L, at least about 30,000 L, at least about 35,000 L, at least about 40,000 L, at least about 45,000 L, at least about 50,000 L, at least about 55,000 L, at least about 60,000 L, at least about 65,000 L, at least about 70,000 L, at least about 75,000 L, at least about 80,000 L, at least about 85,000 L, at least about 90,000 L, at least about 95,000 L, at least about 100,000 L, etc.

In certain embodiments, the yield of gB protein (or immunogenic fragment thereof) from the cell culture is at least about 0.01 g/L, at least about 0.02 g/L, at least about 0.03 g/L, at least about 0.05 g/L, at least about 0.06 g/L, at least about 0.07 g/L, at least about 0.08 g/L, at least about 0.09 g/L, at least about 0.1 g/L, at least about 0.15 g/L, at least about 0.20 g/L, at least about 0.25 g/L, at least about 0.3 g/L, at least about 0.35 g/L, at least about 0.4 g/L, at least about 0.45 g/L, at least about 0.5 g/L, at least about 0.55 g/L, at least about 0.6 g/L, at least about 0.65 g/L, at least about 0.7 g/L, at least about 0.75 g/L, at least about 0.8 g/L, at least about 0.85 g/L, at least about 0.9 g/L, at least about 0.95 g/L, or at least about 1.0 g/L.

Also provided herein is a process of producing cytomegalovirus (CMV) gB protein, or an immunogenic fragment thereof, comprising: (i) culturing the host cell described herein under a suitable condition, thereby expressing said gB protein, or immunogenic fragment thereof; and (ii) harvesting said gB protein, or immunogenic fragment thereof, from the culture.

In certain embodiments, the gB protein (or immunogenic fragment thereof) described herein is purified. The gB protein (or immunogenic fragment thereof) can be purified using any suitable methods, such as HPLC, various types of chromatography (such as hydrophobic interaction, ion exchange, affinity, chelating, and size exclusion), electrophoresis, density gradient centrifugation, solvent extraction, or the like. As appropriate, the gB protein (or immunogenic fragment thereof) may be further purified, as required, so as to remove substantially any proteins which are also secreted in the medium or result from lysis of host cells, so as to provide a product which is at least substantially free of host debris, e.g., proteins, lipids and polysaccharides. See, e.g., those set forth in Sandana (1997) Bioseparation of Proteins, Academic Press, Inc.; and Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, U.K.; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ. If desired, the gB protein (or immunogenic fragment thereof) can include a "tag" that facilitates purification, as described above.

For example, methods for purifying CMV gB protein by immunoaffinity chromatography has been disclosed. Ruiz-Arguello et al., J. Gen. Virol., 85:3677-3687 (2004).

5. Pharmaceutical Compositions and Methods of Treatment

The invention provides pharmaceutical compositions and methods of treatment using the cytomegalovirus (CMV) gB protein (or immunogenic fragments thereof) described herein, or a nucleic acid encoding such gB protein (or immunogenic fragments thereof) described herein. For example, the proteins or immunogenic fragments can be delivered directly as components of an immunogenic composition, or nucleic acids that encode the gB proteins or immunogenic fragments can be administered to produce the CMV protein or immunogenic fragment in vivo. Certain preferred embodiments, such as protein formulations, recombinant nucleic acids (e.g., self-replicating RNA) and alphavirus VRP that contain sequences encoding gB proteins or immunogenic fragments are further described herein.

A. Protein Compositions

In one aspect, the invention provides an immunogenic composition comprising the recombinant CMV gB protein (or immunogenic fragment thereof) described herein.

The immunogenic composition can comprise additional CMV proteins, such as gO, gH, gL, pUL128, pUL130, pUL131, an immunogenic fragment thereof, or a combination thereof. For example, the gB (or immunogenic fragment thereof) can be combined with CMV pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof. The gB (or immunogenic fragment thereof) can also be combined with CMV trimeric complex comprising: gH or a trimer-forming fragment thereof, gL or a trimer-forming fragment thereof, and gO or a trimer-forming fragment thereof.

The immunogenic composition may comprise an adjuvant. Exemplary adjuvants to enhance effectiveness of the composition include: (1) aluminum salts (alum), such as aluminum hydroxide, aluminum phosphate, aluminum sulfate, etc; (2) oil-in-water emulsion formulations (with or without other specific adjuvants such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as adjuvants to enhance the effectiveness of the composition.

Muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acety lmuramyl-L-alanyl-D-isoglutaminyl-L-alanine-2-(1'-2'-dipalmitoyl-sn-glycer o-3-hydroxyphosphoryloxy)-ethylamine (MTP-PE), etc.

In certain embodiment, the adjuvant is an aluminum salt. In certain embodiment, the adjuvant is an oil-in-water emulsion, such as MF59.

In certain embodiment, the adjuvant is a TLR7 agonist, such as imidazoquinoline or imiquimod.

In certain embodiment, the adjuvant is an aluminum salt, such as aluminum hydroxide, aluminum phosphate, aluminum sulfate.

The adjuvants described herein can be used singularly or in any combination, such as alum/TLR7 agonist combination.

B. Alphavirus VRP

In some embodiments, CMV gB proteins (or immunogenic fragments thereof) described herein are delivered using alphavirus replicon particles (VRP). As used herein, the term "alphavirus" has its conventional meaning in the art and includes various species such as Venezuelan equine encephalitis virus (VEE; e.g., Trinidad donkey, TC83CR, etc.), Semliki Forest virus (SFV), Sindbis virus, Ross River virus, Western equine encephalitis virus, Eastern equine encephalitis virus, Chikungunya virus, S.A. AR86 virus, Everglades virus, Mucambo virus, Barmah Forest virus, Middelburg virus, Pixuna virus, O'nyong-nyong virus, Getah virus, Sagiyama virus, Bebaru virus, Mayaro virus, Una virus, Aura virus, Whataroa virus, Banbanki virus, Kyzylagach virus, Highlands J virus, Fort Morgan virus, Ndumu virus, and Buggy Creek virus.

An "alphavirus replicon particle" (VRP) or "replicon particle" is an alphavirus replicon packaged with alphavirus structural proteins.

An "alphavirus replicon" (or "replicon") is an RNA molecule which can direct its own amplification in vivo in a target cell. The replicon encodes the polymerase(s) which catalyze RNA amplification (nsP1, nsP2, nsP3, nsP4) and contains cis RNA sequences required for replication which are recognized and utilized by the encoded polymerase(s). An alphavirus replicon typically contains the following ordered elements: 5' viral sequences required in cis for replication, sequences which encode biologically active alphavirus nonstructural proteins (nsP1, nsP2, nsP3, nsP4), 3' viral sequences required in cis for replication, and a polyadenylate tract. An alphavirus replicon also may contain one or more viral subgenomic "junction region" promoters directing the expression of heterologous nucleotide sequences, which may, in certain embodiments, be modified in order to increase or reduce viral transcription of the subgenomic fragment and heterologous sequence(s) to be expressed. Other control elements can be used, such as IRES or 2A sequences.

C. Nucleic Acid Delivery Systems

Recombinant nucleic acid molecule that encodes the CMV gB proteins or immunogenic fragments described herein can be administered to induce production of the encoded CMV gB proteins or immunogenic fragments and an immune response thereto.

The recombinant nucleic acid can be DNA (e.g., plasmid or viral DNA) or RNA, preferably self-replicating RNA, and can be monocistronic or polycistronic. Any suitable DNA or RNA can be used as the nucleic acid vector that carries the open reading frames that encode CMV gB proteins or immunogenic fragments thereof. Suitable nucleic acid vectors have the capacity to carry and drive expression of one or more CMV gB proteins or immunogenic fragments. Such nucleic acid vectors are known in the art and include, for example, plasmids, DNA obtained from DNA viruses such as vaccinia virus vectors (e.g., NYVAC, see U.S. Pat. No. 5,494,807), and poxvirus vectors (e.g., ALVAC canarypox vector, Sanofi Pasteur), and RNA obtained from suitable RNA viruses such as alphavirus. If desired, the recombinant nucleic acid molecule can be modified, e.g., contain modified nucleobases and or linkages as described further herein.

The self-replicating RNA molecules of the invention are based on the genomic RNA of RNA viruses, but lack the genes encoding one or more structural proteins. The self-replicating RNA molecules are capable of being translated to produce non-structural proteins of the RNA virus and CMV gB proteins encoded by the self-replicating RNA.

The self-replicating RNA generally contains at least one or more genes selected from the group consisting of viral replicase, viral proteases, viral helicases and other nonstructural viral proteins, and also comprise 5'- and 3'-end cis-active replication sequences, and a heterologous sequences that encodes one or more desired CMV gB proteins. A subgenomic promoter that directs expression of the heterologous sequence(s) can be included in the self-replicating RNA. If desired, a heterologous sequence may be fused in frame to other coding regions in the self-replicating RNA and/or may be under the control of an internal ribosome entry site (IRES).

Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinbis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of encoded CMV protein, or may be transcribed to provide further transcripts with the same sense as the delivered RNA which are translated to provide in situ expression of the encoded CMV protein(s).

A preferred self-replicating RNA molecule thus encodes (i) a RNA-dependent RNA polymerase which can transcribe RNA from the self-replicating RNA molecule and (ii) one or more CMV gB proteins or immunogenic fragments thereof. The polymerase can be an alphavirus replicase e.g. comprising alphavirus non-structural proteins nsP1-nsP4.

The self-replicating RNA molecules of the invention can contain one or more modified nucleotides and therefore have improved stability and be resistant to degradation and clearance in vivo, and other advantages. There are more than 96 naturally occurring nucleoside modifications found on mammalian RNA. See, e.g., Limbach et al., Nucleic Acids Research, 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated herein by reference in their entirety, and many modified nucleosides and modified nucleotides are commercially available. If desired, the self-replicating RNA molecule can contain phosphoramidate, phosphorothioate, and/or methylphosphonate linkages.

The self-replicating RNA described herein is suitable for delivery in a variety of modalities, such as naked RNA delivery or in combination with lipids, polymers or other compounds that facilitate entry into the cells. Self-replicating RNA molecules can be introduced into target cells or subjects using any suitable technique, e.g., by direct injection, microinjection, electroporation, lipofection, biolistics, and the like. The self-replicating RNA molecule may also be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine amino acids), which is itself coupled to an integrin receptor-binding moiety (e.g., a cyclic peptide having the sequence Arg-Gly-Asp).

The self-replicating RNA molecules can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

The self-replicating RNA can be delivered as naked RNA (e.g. merely as an aqueous solution of RNA) but, to enhance entry into cells and also subsequent intercellular effects, the self-replicating RNA is preferably administered in combination with a delivery system, such as a particulate or emulsion delivery system. A large number of delivery systems are well known to those of skill in the art. Three particularly useful delivery systems are (i) liposomes, (ii) non-toxic and biodegradable polymer microparticles, and (iii) cationic submicron oil-in-water emulsions.

The invention also provides immunogenic composition comprising the nucleic acid (e.g., self-replicating RNA) described herein. The immunogenic composition may comprise an adjuvant, as described above. Preferred adjuvants include, e.g., an aluminum salt or an oil-in-water emulsion (such as MF59).

D. Pharmaceutical Formulations

Each of the immunogenic compositions discussed herein may be used alone or in combination with one or more other antigens, the latter either from the same viral pathogen or from another pathogenic source or sources. These pharmaceutical formulations may either be prophylactic (to prevent infection) or therapeutic (to treat disease after infection).

Such pharmaceutical formulations comprise an immunogenic composition, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as adjuvants. Furthermore, the antigen may be conjugated to a bacterial toxoid, such as a toxoid from diphtheria, tetanus, cholera, *H. pylori*, etc. pathogens.

The pharmaceutical formulations may comprise an adjuvant, as described above.

The pharmaceutical formulations (e.g., the immunogenic composition, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the pharmaceutical formulations are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Pharmaceutical formulations comprise an immunologically effective amount of the antigenic polypeptides, as well as any other of the above-mentioned components, as needed. By "immunologically effective amount," it is meant that the administration of that amount to an individual, either in a single dose or as part of a series, is effective for treatment or prevention of illness, infection or disease. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctors assessment of the medical situation, and other relevant factors. It is expected that the amount will fall in a relatively broad range that can be determined through routine trials.

The pharmaceutical formulations are conventionally administered parenterally, e.g., by injection, either subcutaneously or intramuscularly. Additional formulations suitable for other modes of administration include oral and pulmonary formulations, suppositories, and transdermal applications. Oral formulations may be preferred for certain viral proteins. Dosage treatment may be a single dose schedule or a multiple dose schedule. The immunogenic composition may be administered in conjunction with other immuno-regulatory agents.

5. Methods of Treatment

In another aspect, the invention provides a method of inducing an immune response against cytomegalovirus (CMV), comprising administering to a subject in need thereof an immunologically effective amount of the immunogenic composition describe herein, which comprises the proteins, DNA molecules, RNA molecules (e.g., self-replicating RNA molecules), or VRPs as described above.

In certain embodiments, the immune response comprises the production of neutralizing antibodies against CMV. In certain embodiments, the neutralizing antibodies are complement-independent.

The immune response can comprise a humoral immune response, a cell-mediated immune response, or both. In some embodiments an immune response is induced against each delivered CMV protein. A cell-mediated immune response can comprise a Helper T-cell (Th) response, a CD8+ cytotoxic T-cell (CTL) response, or both. In some embodiments the immune response comprises a humoral immune response, and the antibodies are neutralizing antibodies. Neutralizing antibodies block viral infection of cells. CMV infects epithelial cells and also fibroblast cells. In some embodiments the immune response reduces or prevents infection of both cell types. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a CMV virus of a strain other than the strain used in the composition.

A useful measure of antibody potency in the art is "50% neutralization titer." To determine 50% neutralizing titer, serum from immunized animals is diluted to assess how dilute serum can be yet retain the ability to block entry of 50% of viruses into cells. For example, a titer of 700 means that serum retained the ability to neutralize 50% of virus after being diluted 700-fold. Thus, higher titers indicate more potent neutralizing antibody responses. In some embodiments, this titer is in a range having a lower limit of about 200, about 400, about 600, about 800, about 1000, about 1500, about 2000, about 2500, about 3000, about 3500, about 4000, about 4500, about 5000, about 5500, about 6000, about 6500, or about 7000. The 50% neutralization titer range can have an upper limit of about 400, about 600, about 800, about 1000, about 1500, about 2000, about 2500, about 3000, about 3500, about 4000, about 4500, about 5000, about 5500, about 6000, about 6500, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, or about 30000. For example, the 50% neutralization titer can be about 3000 to about 6500. "About" means plus or minus 10% of the recited value. Neutralization titer can be measured as described in the specific examples, below.

An immune response can be stimulated by administering proteins, DNA molecules, RNA molecules (e.g., self-replicating RNA molecules), or VRPs to an individual, typically a mammal, including a human. In some embodiments the immune response induced is a protective immune response, i.e., the response reduces the risk or severity of CMV infection. Stimulating a protective immune response is particularly desirable in some populations particularly at risk from CMV infection and disease. For example, at-risk populations include solid organ transplant (SOT) patients, bone marrow transplant patients, and hematopoietic stem cell transplant (HSCT) patients. VRPs can be administered to a transplant donor pre-transplant, or a transplant recipient pre- and/or post-transplant. Because vertical transmission from mother to child is a common source of infecting infants, administering VRPs to a woman who is pregnant or can become pregnant is particularly useful.

Any suitable route of administration can be used. For example, a composition can be administered intramuscularly, intraperitoneally, subcutaneously, or transdermally. Some embodiments will be administered through an intramucosal route such as intra-orally, intra-nasally, intra-vaginally, and intra-rectally. Compositions can be administered according to any suitable schedule.

Also provided herein is a method of inhibiting cytomegalovirus (CMV) entry into a cell, comprising contacting the cell with the immunogenic composition described herein.

This invention is further illustrated by the following examples which should not be construed as limiting.

EXAMPLES

Example 1—Generation of a Soluble gB Construct and Solving the Crystal Structure of HCMV Glycoprotein B Bound to a Human Neutralizing Antibody Fab Fragment The ectodomain of CMV gB, residues 1 to 698, with a 6-His tag (SEQ ID NO: 8) at the C-terminus was expressed in 293GnTI-cells (FIG. 1). The WT ectodomain sequence failed to express as a secreted protein. To increase protein secretion we mutated three hydrophobic residues in the fusion loops with the corresponding amino acids from HSV-1 gB (I157H, H158R and W240R), which are more hydrophilic. We also mutated the canonical furin cleavage site to decrease protein heterogeneity caused by incomplete processing during expression (R457S/R460S), as well as Cys246 to Ser to prevent formation of spurious disulfide bonds (FIG. 1). Despite these changes, size exclusion chromatography (SEC; FIG. 2A) and negative stain EM (data not shown) revealed that the protein (gB-698) formed dimeric trimers of the characteristic three-lobed post-fusion trimers. Analysis of the EM images suggested that dimerization was mediated by the base of the gB trimer, presumably due to the intrinsic hydrophobicity of this surface. Thus, we introduced a glycosylation site in fusion loop-2 (W240N, Y242T), predicted to be solvent exposed in the trimer, to interfere with dimerization of the trimers. EM and SEC confirmed that this construct, gB-698glyc, does not dimerize (to form dimeric trimers) even at high protein concentration (FIG. 2A and data not shown).

Figure 3:
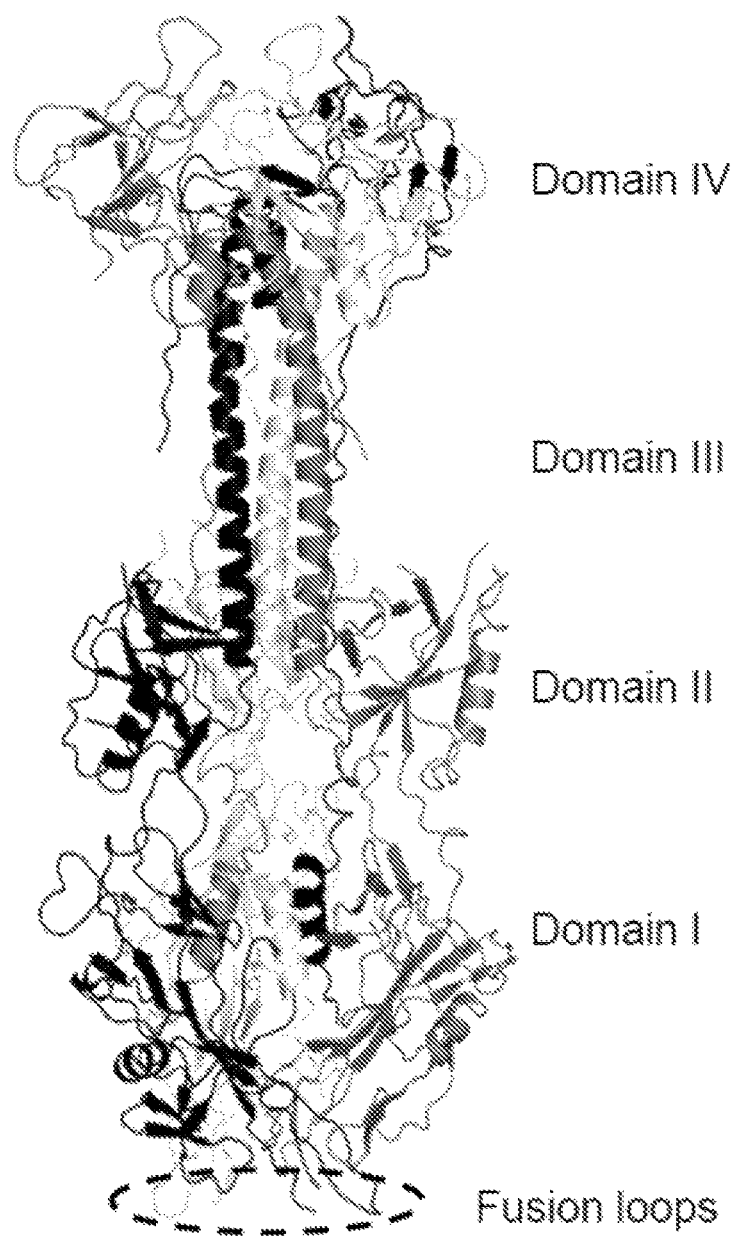
FIG. 3 shows the crystal structure of ΔNgB.

Initial attempts at crystallizing gB-698glyc by itself or in complex with a neutralizing antibody Fab fragment were unsuccessful. We therefore deglycosylated the protein with endoglycosidase H (Endo H) and performed in situ limited proteolysis with subtilisin E to remove flexible regions that could interfere with crystallization. This treatment resulted in crystals that, however, only diffracted up to 4.3 Å resolution. To improve diffraction, we deleted 63 N-terminal residues of the gB ectodomain (ΔNgB, lacking residues 25-86) shown to be flexible in HSV-1 gB (Heldwein et al., Science, 313(5784):217-220, 2006). The deglycosylated ΔNgB-1 G2 Fab complex crystallized readily without need for protease treatment. After screening several crystals, a 3.6 Å resolution data set was obtained and the structure determined by molecular replacement (FIG. 3).

Example 2—CMV gB Mutant Constructs

Figure 4:
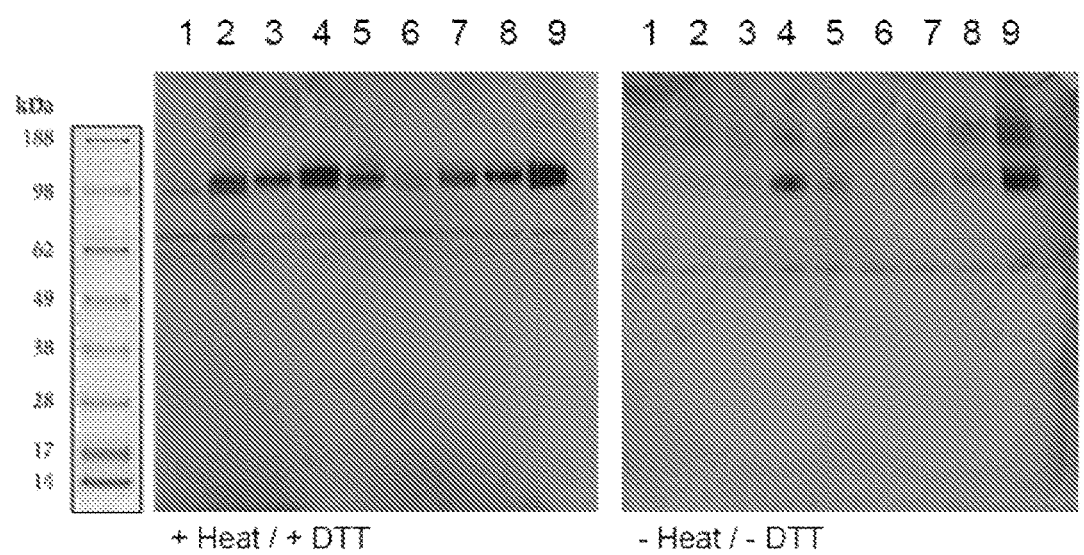
FIG. 4 shows the western blot of cell culture supernatant using anti-His antibody. Lanes: 1: wild type (WT); 2: R236N; 3: G237N; 4: T158N/Y160T; 5: Y160E; 6: R236E/S238E; 7: R236E/S238E/T239E; 8: NGT inserted before W240; 9: I156H/H157R/W240N/Y242T. The left panel shows samples reduced with 50 mM DTT and boiled at 95° C. for 5 minutes. The right panel shows samples under non-boiled and non-reduced conditions. All constructs except wild type gB ectodomain and R236E/S238E had detectable expression under boiled and reduced conditions (left panel).

Based on the crystal structure of gB, we designed mutations within hydrophobic surface (encompassing the two fusion loops and residues in the vicinity of the two fusion loops) to explore mutants that allow the expression of soluble gB ectodomain (monomeric trimer). Mutants were made and tested in an expression experiment. FIG. 4 shows the western blot of cell culture supernatant with anti-His antibody. All constructs except wild type gB ectodomain and R236E/S238E had detectable secreted expression under boiled and reduced conditions (left panel).

The following constructs were made and tested:
1. WT
2. R236N
3. G237N
4. T158N/Y160T
5. Y160E
6. R236E
7. R236E/S238E
8. NGT inserted before W240
9. I156H/H157R/W240N/Y242T (B-698glyc)

All constructs contained the following additional mutations: R457S/R460S (furin cleavage site mutations) and C246S.

T158N/Y160T (lane 4) shows a band at the monomer size under non-boiled/non-reduced conditions similar to gB-698glyc (lane 9). The rest (except lanes 1 and 6) appear to be forming higher order oligomer structures only visible once broken down with heat and DTT. These results indicate that inserting a glycosylation site just following fusion loop 1 is likely sufficient to allow for soluble expression of a gB ectodomain even if the wild type fusion loop residues are present. Having a glycosylation site just outside fusion loop 1 is sufficient to allow secretion without the need to mutate hydrophobic residues within FL1. A glycosylation site outside FL1 achieved results comparable to mutating residues within the fusion loops to add a glycosylation site.

The various features and embodiments of the present invention, referred to in individual sections above apply, as appropriate, to other sections, mutatis mutandis. Consequently features specified in one section may be combined with features specified in other sections, as appropriate.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and GenBank sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

1. A recombinant cytomegalovirus (CMV) gB protein, or an immunogenic fragment thereof, wherein
   (i) said gB protein, or immunogenic fragment thereof, does not comprise a transmembrane (TM) domain; and
   (ii) said gB protein, or immunogenic fragment thereof, comprises a mutation that results in a glycosylation site within hydrophobic surface 1.

2. The recombinant gB protein of embodiment 1, wherein said glycosylation site is an N-glycosylation site comprising N-X-S/T motif, wherein X is any amino acid residue except proline.

3. The recombinant gB protein of embodiment 1 or 2, wherein said mutation is selected from the group consisting of (i) R236N, (ii) G237N, (iii) T158N, (iv) W240N and Y242S, (v) W240N and Y242T, and a combination thereof.

4. The recombinant gB protein of any one of embodiments 1-3, wherein said mutation comprises an insertion of N-X-S/T sequence, wherein X is any amino acid residue except proline.

5. The recombinant gB protein of embodiment 4, wherein said mutation comprises an insertion of N-X-S/T sequence, wherein X is any amino acid residue except proline, in fusion loop 1 (FL1), fusion loop 2 (FL2), or both.

6. The recombinant gB protein of embodiment 5, wherein said mutation comprises an insertion of N-X-S/T sequence, wherein X is any amino acid residue except proline, without mutating other residues in FL1 and FL2.

7. The recombinant gB protein of any one of embodiments 4-6, wherein said mutation comprises mutating $^{236}$RGSTW (SEQ ID NO: 12) to $^{236}$RGSTNGTW (SEQ ID NO: 13); $^{240}$WLYR (SEQ ID NO: 14) to $^{240}$WLYNGTR (SEQ ID NO: 15), or a combination thereof.

8. The recombinant gB protein of any one of embodiments 1-7, further comprising a mutation that results in a reduction of overall hydrophobicity index of said hydrophobic surface 1.

9. The recombinant gB protein of embodiment 8, wherein (i) said mutation comprises replacing a hydrophobic amino acid residue with an amino acid residue that comprises a charged side chain or a polar side chain; or (ii) said mutation is at residue I156 (e.g., I156H), H157 (e.g., H157R), or a combination thereof.

10. The recombinant gB protein of embodiment 9, wherein said hydrophobic amino acid residue is selected from the group consisting of: A, V, L, I, P, M, F, G, and W.

11. The recombinant gB protein of embodiment 9 or 10, wherein said amino acid residue comprising a charged side chain is selected from the group consisting of D, E, K, R, and H.

12. The recombinant gB protein of embodiment 9 or 10, wherein said amino acid residue comprising a polar side chain is selected from the group consisting of S, T, C, N, Q, and Y.

13. The recombinant gB protein of embodiment 8, wherein said mutation comprises deleting a hydrophobic amino acid residue within hydrophobic surface 1.

14. The recombinant gB protein of embodiment 13, wherein said hydrophobic amino acid residue is selected from the group consisting of: A, V, L, I, P, M, F, G, and W.

15. The recombinant gB protein of embodiment 8, wherein said mutation comprises inserting an amino acid residue that comprises a charged side chain or a polar side chain within hydrophobic surface 1.

16. The recombinant gB protein of embodiment 15, wherein said amino acid residue comprising a charged side chain is selected from the group consisting of D, E, K, R, and H.

17. The recombinant gB protein of embodiment 15, wherein said amino acid residue comprising a polar side chain is selected from the group consisting of S, T, C, N, Q, and Y.

18. The recombinant gB protein of any one of embodiments 1-17, comprising a mutation that replaces Y160 with an amino acid residue that comprises a charged side chain or a polar side chain.

19. The recombinant gB protein of embodiment 18, wherein said amino acid residue comprising a charged side chain is selected from the group consisting of D, E, K, R, and H.

20. The recombinant gB protein of embodiment 18 or 19, comprising a Y160E mutation.

21. The recombinant gB protein of embodiment 18, wherein said amino acid residue comprising a polar side chain is selected from the group consisting of S, T, C, N, and Q.

22. The recombinant gB protein of embodiment 18 or 21, comprising a Y160T mutation.

23. The recombinant gB protein of any one of embodiments 1-18 and 21-22, comprising $^{158}$TTY$^{160}$ to $^{158}$NTT$^{160}$ mutation.

24. The recombinant gB protein of any one of embodiments 1-23, comprising a mutation that replaces S238 with an amino acid residue that comprises a charged side chain.

25. The recombinant gB protein of embodiment 24, wherein said amino acid residue comprising a charged side chain is selected from the group consisting of D, E, K, R, and H.

26. The recombinant gB protein of embodiment 25, comprising a S238E mutation.

27. The recombinant gB protein of any one of embodiments 1-26, comprising a mutation that replaces T239 with an amino acid residue that comprises a charged side chain.

28. The recombinant gB protein of embodiment 27, wherein said amino acid residue comprising a charged side chain is selected from the group consisting of D, E, K, R, and H.

29. The recombinant gB protein of embodiment 28, comprising a T239E mutation.

30. The recombinant gB protein of any one of embodiments 1-29, comprising a S238E mutation and a T239E mutation.
31. The recombinant gB protein of any one of embodiments 1-30, comprising an R236E mutation or R236D mutation.
32. The recombinant gB protein of embodiment 31, wherein said mutation is an R236E mutation.
33. The recombinant gB protein of any one of embodiments 1-32, comprising mutations selected from the group consisting of: (i) R236E and S238E; (ii) R236E and T239E; and (iii) R236E, S238E, and T239E.
34. A recombinant cytomegalovirus (CMV) gB protein, or an immunogenic fragment thereof, wherein
  (i) said gB protein, or immunogenic fragment thereof, does not comprise a transmembrane (TM) domain; and
  (ii) said gB protein, or immunogenic fragment thereof, comprises a mutation that results in a glycosylation site, wherein said glycosylation site is (1) within hydrophobic surface 2; or (2) at a residue that is within 20 angstroms from fusion loop 1 (FL1) or fusion loop 2 (FL2).
35. The recombinant gB protein of embodiment 34, wherein said glycosylation site is an N-glycosylation site comprising N-X-S/T motif, wherein X is any amino acid residue except proline.
36. The recombinant gB protein of embodiment 34 or 35, wherein said mutation comprises an insertion of N-X-S/T sequence, wherein X is any amino acid residue except proline.
37. The recombinant gB protein of any one of embodiments 34-36, wherein said glycosylation site is at a residue that is within 10 angstroms from fusion loop 1 (FL1) or fusion loop 2 (FL2).
38. The recombinant gB protein of any one of embodiments 34-37, wherein said mutation is within residues 696-698.
39. The recombinant gB protein of any one of embodiments 34-38, further comprising a mutation that results in a reduction of overall hydrophobicity index of said hydrophobic surface 2.
40. The recombinant gB protein of any one of embodiments 34-39, further comprising a mutation that results in a reduction of overall hydrophobicity index of hydrophobic surface 1.
41. The recombinant gB protein of embodiment 39 or 40, wherein (i) said mutation comprises replacing a hydrophobic amino acid residue with an amino acid residue that comprises a charged side chain or a polar side chain; or (ii) said mutation is at residue 1156 (e.g., 1156H), H157 (e.g., H157R), or a combination thereof.
42. The recombinant gB protein of embodiment 41, wherein said hydrophobic amino acid residue is selected from the group consisting of: A, V, L, I, P, M, F, G, and W.
43. The recombinant gB protein of embodiment 41 or 42, wherein said amino acid residue comprising a charged side chain is selected from the group consisting of D, E, K, R, and H.
44. The recombinant gB protein of embodiment 41 or 42, wherein said amino acid residue comprising a polar side chain is selected from the group consisting of S, T, C, N, Q, and Y.
45. The recombinant gB protein of embodiment 39 or 40, wherein said mutation comprises deleting a hydrophobic amino acid residue.
46. The recombinant gB protein of embodiment 45, wherein said hydrophobic amino acid residue is selected from the group consisting of: A, V, L, I, P, M, F, G, and W.
47. The recombinant gB protein of embodiment 39 or 40, wherein said mutation comprises inserting an amino acid residue that comprises a charged side chain or a polar side chain.
48. The recombinant gB protein of embodiment 47, wherein said amino acid residue comprising a charged side chain is selected from the group consisting of D, E, K, R, and H.
49. The recombinant gB protein of embodiment 47, wherein said amino acid residue comprising a polar side chain is selected from the group consisting of S, T, C, N, Q, and Y.
50. A recombinant cytomegalovirus (CMV) gB protein, or an immunogenic fragment thereof, wherein
  (i) said gB protein, or immunogenic fragment thereof, does not comprise a transmembrane (TM) domain; and
  (ii) said gB protein, or immunogenic fragment thereof, comprises a mutation in a hydrophobic surface 1, wherein said mutation results in a reduction of overall hydrophobicity index of said hydrophobic surface 1; wherein said mutation is not a deletion or substitution of an amino acid in fusion loop 1 (FL1) and fusion loop 2 (FL2).
51. The recombinant gB protein of embodiment 50, wherein said mutation comprises replacing a hydrophobic amino acid residue with an amino acid residue that comprises a charged side chain or a polar side chain.
52. The recombinant gB protein of embodiment 51, wherein said hydrophobic amino acid residue is selected from the group consisting of: A, V, L, I, P, M, F, G, and W.
53. The recombinant gB protein of embodiment 51 or 52, wherein said amino acid residue comprising a charged side chain is selected from the group consisting of D, E, K, R, and H.
54. The recombinant gB protein of embodiment 51 or 52, wherein said amino acid residue comprising a polar side chain is selected from the group consisting of S, T, C, N, Q, and Y.
55. The recombinant gB protein of embodiment 50, wherein said mutation comprises deleting a hydrophobic amino acid residue.
56. The recombinant gB protein of embodiment 55, wherein said hydrophobic amino acid residue is selected from the group consisting of: A, V, L, I, P, M, F, G, and W.
57. The recombinant gB protein of embodiment 50, wherein said mutation comprises inserting an amino acid residue that comprises a charged side chain or a polar side chain.
58. The recombinant gB protein of embodiment 57, wherein said amino acid residue comprising a charged side chain is selected from the group consisting of D, E, K, R, and H.
59. The recombinant gB protein of embodiment 57, wherein said amino acid residue comprising a polar side chain is selected from the group consisting of S, T, C, N, Q, and Y.
60. The recombinant gB protein of any one of embodiments 50-59, comprising a mutation that replaces Y160 with an amino acid residue that comprises a charged side chain or a polar side chain.
61. The recombinant gB protein of embodiment 60, wherein said amino acid residue comprising a charged side chain is selected from the group consisting of R, K, D, and E.
62. The recombinant gB protein of embodiment 61, comprising a Y160E mutation.
63. The recombinant gB protein of embodiment 60, wherein said amino acid residue comprising a polar side chain is selected from the group consisting of S, T, C, N, and Q.
64. The recombinant gB protein of embodiment 61, comprising a Y160T mutation.

65. The recombinant gB protein of any one of embodiment 50-60 and 63-64, comprising $^{158}$TTY$^{160}$ to $^{158}$NTT$^{160}$ mutation.
66. The recombinant gB protein of any one of embodiments 50-65, comprising a mutation that replaces S238 with an amino acid residue that comprises a charged side chain.
67. The recombinant gB protein of embodiment 66, wherein said amino acid residue comprising a charged side chain is selected from the group consisting of R, K, D, and E.
68. The recombinant gB protein of embodiment 67, comprising a S238E mutation.
69. The recombinant gB protein of any one of embodiments 50-68, comprising a mutation that replaces T239 with an amino acid residue that comprises a charged side chain.
70. The recombinant gB protein of embodiment 69, wherein said amino acid residue comprising a charged side chain is selected from the group consisting of R, K, D, and E.
71. The recombinant gB protein of embodiment 70, comprising a T239E mutation.
72. The recombinant gB protein of any one of embodiments 50-71, comprising a S238E mutation and a T239E mutation.
73. The recombinant gB protein of any one of embodiments 50-72, comprising an R236E mutation or R236D mutation.
74. The recombinant gB protein of embodiment 73, wherein said mutation is an R236E mutation.
75. The recombinant gB protein of any one of embodiments 50-72, comprising mutations selected from the group consisting of: (i) R236E and S238E; (ii) R236E and T239E; and (iii) R236E, S238E, and T239E.
76. The recombinant gB protein of any one of embodiments 1-75, comprising a heterologous sequence that is at least 12 residues long at the C-terminus.
77. The recombinant CMV gB protein of embodiment 76, wherein said heterologous sequence is at least 20 residues long.
78. The recombinant CMV gB protein of embodiment 76 or 77, wherein said heterologous sequence comprises an amphipathic peptide.
79. A recombinant cytomegalovirus (CMV) gB protein, or an immunogenic fragment thereof, wherein
    (i) said gB protein, or immunogenic fragment thereof, does not comprise a transmembrane (TM) domain;
    (ii) said gB protein, or immunogenic fragment thereof, comprises an ectodomain; and (iii) said gB protein, or immunogenic fragment thereof, comprises a heterologous sequence that is at least 12 residues long at the C-terminus.
80. The recombinant CMV gB protein of embodiment 79, wherein said heterologous sequence is at least 20 residues long.
81. The recombinant CMV gB protein of embodiment 79 or 80, wherein said heterologous sequence comprises an amphipathic peptide.
82. A CMV complex comprising the recombinant gB protein of any one of embodiments 1-81.
83. The CMV complex of embodiment 82, wherein said complex is a monomeric trimer consisting of three gB protein subunits.
84. An immunogenic composition comprising the recombinant CMV gB protein of any of one of embodiments 1-81, or the complex of embodiment 82 or 83.
85. The immunogenic composition of embodiment 84, further comprising a CMV protein selected from the group consisting of gH, gL, pUL128, pUL130, pUL131, gO, an immunogenic fragment thereof, and a combination thereof.
86. The immunogenic composition of embodiment 84 or 85, further comprising CMV pentameric complex comprising:
gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof.
87. The immunogenic composition of any one of embodiments 84-86, further comprising an adjuvant.
88. The immunogenic composition of embodiment 86, wherein said adjuvant comprises an aluminum salt, a TLR7 agonist, or an oil-in-water emulsion.
89. The immunogenic composition of embodiment 88, wherein said oil-in-water emulsion is MF59.
90. An isolated nucleic acid comprising a polynucleotide sequence encoding the recombinant CMV gB protein of any one of embodiments 1-81.
91. The isolated nucleic acid of embodiment 90, wherein said isolated nucleic acid is an RNA, preferably a self-replicating RNA.
92. The isolated nucleic acid of embodiment 91, wherein said self-replicating RNA is an alphavirus replicon.
93. An alphavirus replication particle (VRP) comprising the alphavirus replicon of embodiment 92.
94. An immunogenic composition comprising the nucleic acid of any one of embodiments 90-92.
95. An immunogenic composition comprising the VRP of embodiment 93.
96. The immunogenic composition of embodiment 94 or 95, further comprising an adjuvant.
97. The immunogenic composition of embodiment 96, wherein said adjuvant comprises an aluminum salt.
98. The immunogenic composition of embodiment 96, wherein said adjuvant comprises an oil-in-water emulsion.
99. The immunogenic composition of embodiment 98, wherein said oil-in-water emulsion is MF59.
100. A host cell comprising the nucleic acid of any one of embodiments 90-92.
101. The host cell of embodiment 100, wherein said nucleic acid is a DNA.
102. The host cell of embodiment 101, wherein said host cell is a mammalian cell.
103. The host cell of embodiment 102, wherein said mammalian cell is a CHO cell or HEK-293 cell.
104. The host cell of any one of embodiments 101-103, wherein said DNA encoding the CMV gB protein or immunogenic fragment thereof is stably integrated into the genome of said host cell.
105. The host cell of any one of embodiments 101-104, wherein when cultured under a suitable condition, said nucleic acid expresses a gB protein that forms a monomeric trimer.
106. The host cell of embodiment 105, wherein said trimer is secreted from the host cell.
107. A cell culture comprising the host cell of embodiments 101-106, wherein said culture is at least 20 liter in size.
108. A cell culture comprising the host cell of embodiments 101-107, wherein said culture is at least 100 liter in size.
109. A cell culture comprising the host cell of embodiments 101-106, wherein said culture, wherein the yield of gB protein is at least 0.05 g/L.
110. A cell culture comprising the host cell of embodiments 101-106, wherein said culture, wherein the yield of gB protein is at least 0.1 g/L.
111. A process of producing a recombinant cytomegalovirus (CMV) gB protein, or an immunogenic fragment thereof, comprising:

(i) culturing the host cell of any one of embodiments 100-106 under a suitable condition, thereby expressing said gB protein, or immunogenic fragment thereof; and
(ii) harvesting said gB protein, or immunogenic fragment thereof, from the culture.

112. The process of embodiment 111, further comprising purifying said recombinant gB protein or immunogenic fragment thereof.

113. A recombinant cytomegalovirus (CMV) gB protein, or an immunogenic fragment thereof, produced by the process of embodiment 111 or 112.

114. A method of inducing an immune response against cytomegalovirus (CMV), comprising administering to a subject in need thereof an immunologically effective amount of the immunogenic composition of any one of embodiments 84-89 and 94-99.

115. The method of embodiment 114, wherein the immune response comprises the production of neutralizing antibodies against CMV.

116. The method of embodiment 115 wherein the neutralizing antibodies are complement-independent.

117. A method of inhibiting cytomegalovirus (CMV) entry into a cell, comprising contacting the cell with the immunogenic composition of any one of embodiments 84-89 and 94-99.

118. The immunogenic composition of any one of embodiments 84-89 and 94-99 for use in inducing an immune response against cytomegalovirus (CMV).

118. Use of the immunogenic composition of any one of embodiments 84-89 and 94-99 for inducing an immune response against cytomegalovirus (CMV).

119. Use of the immunogenic composition of any one of embodiments 84-89 and 94-99 in the manufacture of a medicament for inducing an immune response against cytomegalovirus (CMV).

```
Amino acid sequence of Merlin strain of human Cytomegalovirus gB
protein
                                                         (SEQ ID NO: 1)
         10         20         30         40         50         60
MESRIWCLVV CVNLCIVCLG AAVSSSSTRG TSATHSHHSS HTTSAAHSRS GSVSQRVTSS 70         80         90        100        110        120
QTVSHGVNET IYNTTLKYGD VVGVNTTKYP YRVCSMAQGT DLIRFERNIV CTSMKPINED 130        140        150        160        170        180
LDEGIMVVYK RNIVAHTFKV RVYQKVLTFR RSYAYIHTTY LLGSNTEYVA PPMWEIHHIN 190        200        210        220        230        240
SHSQCYSSYS RVIAGTVFVA YHRDSYENKT MQLMPDDYSN THSTRYVTVK DQWHSRGSTW 250        260        270        280        290        300
LYRETCNLNC MVTITTARSK YPYHFFATST GDVVDISPFY NGTNRNASYF GENADKFFIF 310        320        330        340        350        360
PNYTIVSDFG RPNSALETHR LVAFLERADS VISWDIQDEK NVTCQLTFWE ASERTIRSEA 370        380        390        400        410        420
EDSYHFSSAK MTATFLSKKQ EVNMSDSALD CVRDEAINKL QQIFNTSYNQ TYEKYGNVSV 430        440        450        460        470        480
FETTGGLVVF WQGIKQKSLV ELERLANRSS LNLTHNRTKR STDGNNATHL SNMESVHNLV 490        500        510        520        530        540
YAQLQFTYDT LRGYINRALA QIAEAWCVDQ RRTLEVFKEL SKINPSAILS AIYNKPIAAR 550        560        570        580        590        600
FMGDVLGLAS CVTINQTSVK VLRDMNVKES PGRCYSRPVV IFNFANSSYV QYGQLGEDNE 610        620        630        640        650        660
ILLGNHRTEE CQLPSLKIFI AGNSAYEYVD YLFKRMIDLS SISTVDSMIA LDIDPLENTD 670        680        690        700        710        720
FRVLELYSQK ELRSSNVFDL EEIMREFNSY KQRVKYVEDK VVDPLPPYLK GLDDLMSGLG 730        740        750        760        770        780
AAGKAVGVAI GAVGGAVASV VEGVATFLKN PFGAFTIILV AIAVVIITYL IYTRQRRLCT 790        800        810        820        830        840
QPLQNLFPYL VSADGTTVTS GSTKDTSLQA PPSYEESVYN SGRKGPGPPS SDASTAAPPY 850        860        870        880        890        900
TNEQAYQMLL ALARLDAEQR AQQNGTDSLD GRTGTQDKGQ KPNLLDRLRH RKNGYRHLKD

907
SDEEENV

Amino acid sequence of AD169 strain of human Cytomegalovirus gB
protein
                                                         (SEQ ID NO: 2)
         10         20         30         40         50         60
MESRIWCLVV CVNLCIVCLG AAVSSSSTSH ATSSTHNGSH TSRTTSAQTR SVYSQHVTSS
```

-continued

```
              70         80         90        100        110        120
       EAVSHRANET IYNTTLKYGD VVGVNTTKYP YRVCSMAQGT DLIRFERNII CTSMKPINED 130        140        150        160        170        180
       LDEGIMVVYK RNIVAHTFKV RVYQKVLTFR RSYAYIYTTY LLGSNTEYVA PPMWEIHHIN 190        200        210        220        230        240
       KFAQCYSSYS RVIGGTVFVA YHRDSYENKT MQLIPDDYSN THSTRYVTVK DQWHSRGSTW 250        260        270        280        290        300
       LYRETCNLNC MLTITTARSK YPYHFFATST GDVVYISPFY NGTNRNASYF GENADKFFIF 310        320        330        340        350        360
       PNYTIVSDFG RPNAAPETHR LVAFLERADS VISWDIQDEK NVTCQLTFWE ASERTIRSEA 370        380        390        400        410        420
       EDSYHFSSAK MTATFLSKKQ EVNMSDSALD CVRDEAINKL QQIFNTSYNQ TYEKYGNVSV 430        440        450        460        470        480
       FETSGGLVVF WQGIKQKSLV ELERLANRSS LNITHRTRRS TSDNNTTHLS SMESVHNLVY 490        500        510        520        530        540
       AQLQFTYDTL RGYINRALAQ IAEAWCVDQR RTLEVFKELS KINPSAILSA IYNKPIAARF 550        560        570        580        590        600
       MGDVLGLASC VTINQTSVKV LRDMNVKESP GRCYSRPVVI FNFANSSYVQ YGQLGEDNEI 610        620        630        640        650        660
       LLGNHRTEEC QLPSLKIFIA GNSAYEYVDY LFKRMIDLSS ISTVDSMIAL DIDPLENTDF 670        680        690        700        710        720
       RVLELYSQKE LRSSNVFDLE EIMREFNSYK QRVKYVEDKV VDPLPPYLKG LDDLMSGLGA 730        740        750        760        770        780
       AGKAVGVAIG AVGGAVASVV EGVATFLKNP FGAFTIILVA IAVVIITYLI YTRQRRLCTQ 790        800        810        820        830        840
       PLQNLFPYLV SADGTTVTSG STKDTSLQAP PSYEESVYNS GRKGPGPPSS DASTAAPPYT 850        860        870        880        890        900
       NEQAYQMLLA LARLDAEQRA QQNGTDSLDG QTGTQDKGQK PNLLDRLRHR KNGYRHLKDS

906
       DEEENV
```

---

The invention claimed is:

1. A recombinant cytomegalovirus (CMV) gB protein, or an immunogenic fragment thereof, wherein
   (i) said gB protein, or immunogenic fragment thereof, does not comprise a transmembrane (TM) domain;
   (ii) said gB protein, or immunogenic fragment thereof, comprises a hydrophobic surface 1 that corresponds to amino acid residues 154-160 and 236-243 of SEQ ID NO: 1 which comprises a mutation that results in a glycosylation site within said hydrophobic surface 1, but wherein the mutation is not a substitution of one amino acid in fusion loop 1 (FL1) which corresponds to amino acid residues 155-157 of SEQ ID NO: 1.

2. The recombinant gB protein of claim 1, wherein said glycosylation site is an N-glycosylation site comprising N-X-S/T motif, wherein X is any amino acid residue except proline.

3. The recombinant gB protein of claim 1, wherein said mutation in the hydrophobic surface 1 is selected from the group consisting of (i) R236N, (ii) G237N, (iii) T158N and Y160T, (iv) W240N and Y242S, (v) W240N and Y242T, and a combination thereof.

4. The recombinant gB protein of claim 1, wherein said mutation comprises an insertion of N-X-S/T sequence, wherein X is any amino acid residue except proline, in fusion loop 2 (FL2) which corresponds to amino acid residues 240-242 of SEQ ID NO: 1, or both FL2 and FL1.

5. The recombinant gB protein of claim 1, further comprising a mutation that results in a reduction of overall hydrophobicity index of said hydrophobic surface 1.

6. The recombinant gB protein of claim 1, wherein the mutation in the hydrophobic surface 1 is at I156 and H157, R236, S238, T239, W240, Y242, or a combination thereof.

7. A recombinant cytomegalovirus (CMV) gB protein, or an immunogenic fragment thereof, wherein
   (i) said gB protein, or immunogenic fragment thereof, does not comprise a transmembrane (TM) domain; and
   (ii) said gB protein, or immunogenic fragment thereof, comprises a mutation in hydrophobic surface 1 at amino acid residues 154, 158-160, 236-239, or 243 of SEQ ID NO: 1, wherein said mutation results in a reduction of overall hydrophobicity index of said hydrophobic surface 1.

8. The recombinant gB protein of claim 7, wherein said mutation comprises replacing a hydrophobic amino acid residue with an amino acid residue that comprises a charged side chain or a polar side chain.

9. An immunogenic composition comprising the recombinant gB protein of claim 1, and optionally an adjuvant.

10. A method of inducing an immune response against cytomegalovirus (CMV), comprising administering to a subject in need thereof an immunologically effective amount of the immunogenic composition of claim 9.

11. An isolated nucleic acid comprising a polynucleotide sequence encoding the recombinant CMV gB protein, or immunogenic fragment thereof, of claim 1.

12. An isolated host cell comprising the isolated nucleic acid of claim 11.

13. An isolated nucleic acid comprising a polynucleotide sequence encoding the recombinant CMV gB protein, or immunogenic fragment thereof, of claim 7.

14. An isolated host cell comprising the isolated nucleic acid of claim 13.

15. An immunogenic composition comprising the recombinant gB protein claim 7, and optionally an adjuvant.

16. A method of inducing an immune response against cytomegalovirus (CMV), comprising administering to a subject in need thereof an immunologically effective amount of the immunogenic composition of claim 15.

17. The recombinant gB protein of claim 6, wherein the mutation is at I156H, H157R, W240N, and Y242T.

* * * * *